US009086425B2

(12) United States Patent
Hazen et al.

(10) Patent No.: US 9,086,425 B2
(45) Date of Patent: Jul. 21, 2015

(54) CARBAMYLATED PROTEINS AND RISK OF CARDIOVASCULAR DISEASE

(75) Inventors: Stanley L. Hazen, Pepper Pike, OH (US); Zeneng Wang, Cleveland, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 1061 days.

(21) Appl. No.: 12/674,715

(22) PCT Filed: Aug. 28, 2008

(86) PCT No.: PCT/US2008/074557
§ 371 (c)(1),
(2), (4) Date: Jan. 18, 2011

(87) PCT Pub. No.: WO2009/032722
PCT Pub. Date: Mar. 12, 2009

(65) Prior Publication Data
US 2011/0104818 A1 May 5, 2011

Related U.S. Application Data

(60) Provisional application No. 60/968,688, filed on Aug. 29, 2007, provisional application No. 60/967,431, filed on Sep. 5, 2007, provisional application No. 60/970,641, filed on Sep. 7, 2007.

(51) Int. Cl.
*G01N 33/53* (2006.01)
*G01N 33/92* (2006.01)
*G01N 33/68* (2006.01)

(52) U.S. Cl.
CPC ............ *G01N 33/92* (2013.01); *G01N 33/6812* (2013.01); *G01N 33/6854* (2013.01); *G01N 2333/75* (2013.01); *G01N 2333/765* (2013.01); *G01N 2800/32* (2013.01)

(58) Field of Classification Search
None
See application file for complete search history.

(56) References Cited

U.S. PATENT DOCUMENTS

| 6,040,147 | A | 3/2000 | Ridker et al. | |
| 7,771,954 | B2 * | 8/2010 | Hazen et al. | 435/7.1 |
| 2003/0045004 | A1 | 3/2003 | Barri et al. | |
| 2006/0286106 | A1 * | 12/2006 | Hazen et al. | 424/145.1 |

FOREIGN PATENT DOCUMENTS

| WO | 03/088814 | 10/2003 |
| WO | 2009/32722 | 3/2009 |

OTHER PUBLICATIONS

International Search Report and Written Opinion from PCT/US08/74557 dated Jan. 26, 2009.

Abu-Soud, H.M. & Hazen, S.L. "Nitric oxide is a physiological substrate for mammalian peroxidases," J Biol Chem, 275, 37524-32 (2000).
Anderson et al., "Cardiovascular disease risk profiles," Am Heart J, 121, 293-8 (1991).
Asselbergs et al., "Myeloperoxidase polymorphism related to cardiovascular events in coronary artery disease," Am J Med, 116, 429-30 (2004).
Baldus et al. "Myeloperoxidase enhances nitric oxide catabolism during myocardial ischemia and reperfusion," Free Radio Biol Med, 37, 902-11 (2004).
Bobb, D. & Hofstee, B.H. "Gel isoelectric focusing for following the successive carbamylations of amino groups in chymotrypsinogen A," Anal Biochem, 40, 209-17 (1971).
Brennan et al. "A tale of two controversies: defining both the role of peroxidases in nitrotyrosine formation in vivo using eosinophil peroxidase and myeloperoxidase-deficient mice, and the nature of peroxidase-generated reactive nitrogen species," J Biol Chem, 277, 17415-27 (2002).
Brennan et al., "Prognostic value of myeloperoxidase in patients with chest pain," N Engl J Med, 349, 1595-604 (2003).
Castellani et al., "Transgenic mice express human MPO-463G/A alleles at atherosclerotic lesions, developing hyperlipidemia and obesity in -463G males," J Lipid Res, 47, 1366-77 (2006).
Eiserich et al., "Myeloperoxidase, a leukocyte-derived vascular NO oxidase," Science, 296, 2391-4 (2002).
Erill et al., "Plasma protein carbamylation and decreased acidic drug protein binding in uremia," Clin Pharmacol Ther, 27, 612-8 (1980).
Fluckinger et al., "Hemoglobin carbamylation in uremia," N Engl J Med, 304, 823-7 (1981).
Harrison's Principles of Experimental Medicine, 15th Edition, McGraw-Hill, Inc., NY, 3 pgs., 2001.
Hazen, S.L. & Heinecke, J.W., "3-Chlorotyrosine, a specific marker of myeloperoxidase-catalyzed oxidation, is markedly elevated in low density lipoprotein isolated from human atherosclerotic intima," J Clin Invest, 99, 2075-81 (1997).
Horkko et al., "Carbamylation-induced alterations in low-density lipoprotein metabolism," Kidney Int, 41, 1175-81 (1992).
Husgafvel-Pursiainen et al., "Passive smoking at work: biochemical and biological measures of exposure to environmental tobacco smoke," Int Arch Occup Environ Health, 59, 337-45 (1987).
Kersten et al., "Thiocyanate as a cofactor in myeloperoxidase activity against *Streptococcus mutans*," J Dent Res, 60, 831-7 (1981).

(Continued)

*Primary Examiner* — Gary W Counts
(74) *Attorney, Agent, or Firm* — Calfee, Halter & Griswold LLP

(57) ABSTRACT

Methods for characterizing a test subject's, particularly a human test subject's, risk of having cardiovascular disease or developing cardiovascular disease are provided. Also provided are methods for characterizing a test subject's risk of experiencing a complication of cardiovascular disease near term. The methods comprise determining levels of one or more carbamylated biomarkers in a bodily fluid of the test subject and/or comparing these levels with a reference value. In certain embodiments, the carbamylated biomarkers are carbamylated albumin, carbamylated fibrinogen, carbamylated immunoglobulin and carbamylated apolipoprotein A. In other embodiments, particularly where the test subject does not have clinical evidence of renal disease, the carbamylated biomarker is free and/or total peptide-bound homocitrulline.

6 Claims, 6 Drawing Sheets

(56) References Cited

OTHER PUBLICATIONS

Knapp et al. (1992), Clinical Epidemiology and Biostatics, Williams and Wilkins, Harual Publishing Co., Malvern, PA, 8 pgs.
Kraus, L.M. & Kraus, A.P., Jr., "Carbamoylation of amino acids and proteins in uremia," Kidney Int Suppl, 78, S102-7 (2001).
Kumar et al., "Peroxisome proliferator-activated receptor gamma ligands regulate myeloperoxidase expression in macrophages by an estrogen-dependent mechanism involving the -463GA promoter polymorphism," J Biol Chem, 279, 8300-15 (2004).
Lhotta et al. "Complement C4 phenotypes in patients with end-stage renal disease," Nephron 72, 442-6 (1996).
McMillen et al., "Expression of human myeloperoxidase by macrophages promotes atherosclerosis in mice," Circulation, 111, 2798-804 (2005).
Mun, K.C. & Golper, T.A., "Impaired biological activity of erythropoietin by cyanate carbamylation," Blood Purif, 18, 13-7 (2000).
Nicholls, S.J. & Hazen, S.L., "Myeloperoxidase and cardiovascular disease," Arterioscler Thromb Vasc Biol, 25, 1102-11 (2005).
Nicholls, et al., "Cardiac Function and Heart Failure", J of the American College of Cardiology, Elsevier, NY, NY, pp. A35-A82, 2008.
Nielson et al., "Quantitative determination of human fibrinogen in plasma following carbamylation by laurell electrophoresis in antibody containing gel", Clinica Chimica Acta, Elsevier, BV, Amsterdam, NL, vol. 25, No. 1, Dec. 1, 1971, pp. 281-284.
Ok et al., "Carbamylated low-density lipoprotein induces death of endothelial cells: a link to atherosclerosis in patients with kidney disease," Kidney Int, 68, 173-8 (2005).
Olea, F. & Parras, P., "Determination of serum levels of dietary thiocyanate," J Anal Toxicol 16, 258-60 (1992).
Podrez et al., "Myeloperoxidase-generated reactive nitrogen species convert LDL into an atherogenic form in vitro," J Clin Invest, 103, 1547-60 (1999).
Shao et al., "Tyrosine 192 in apolipoprotein A-I is the major site of nitration and chlorination by myeloperoxidase, but only chlorination markedly impairs ABCA1-dependent cholesterol transport," J Biol Chem, 280, 5983-93 (2005).
Stark et al., "Reactions of the cyanante present in aqueous urea with amino acids and proteins," J Biol Chem, 235, 3177-81 (1960).
Stark, G.R. & Smyth, D.G., "The use of cyanate for the determination of NH2-terminal residues in proteins," J Biol Chem, 238, 214-26 (1963).
Stark, G.R., "On the reversible reaction of cyanate with sulfhydryl groups and the determination of NH2-terminal cysteine and cystine in proteins," J Biol Chem, 239, 1411-4 (1964).
Stark, G.R., "Reactions of Cyanate with Functional Groups of Proteins. II. Formation, Decomposition, and Properties of N-Carbamylimidazole," Biochemistry, 4, 588-95 (1965).
Steinbrecher et al., "Immunogenicity of homologous low density lipoprotein after methylation, ethylation, acetylation, or carbamylation: generation of antibodies specific for derivatized lysine," J. of Lipid Research, vol. 25, No. 10, pp. 1109-1116 (1984).
Stephan et al., "Rapid Fluorometric assay of LDL receptor activity by Dillabeled LDL," J Lipid Res 34, 325-330 (1993).
Stim, J. et al., "Factors determining hemoglobin carbamylation in renal failure," Kidney Int, 48, 1605-10 (1995).
Stoves et al., "MDRD equation estimates of glomerular filtration rate in potential living kidney donors and renal transplant recipients with impaired graft function," Nephrol Dial Transplant, 17, 2036-7 (2002).
Thukkani et al. "Identification of alpha-chloro fatty aldehydes and unsaturated lysophosphatidylcholine molecular species in human atherosclerotic lesions," Circulation, 108, 3128-33 (2003).
Van Dalen et al., "Thiocyanate and chloride as competing substrates for myeloperoxidase," Biochem J, 327 (Pt 2), 487-92 (1997).
Vita et al., "Serum myeloperoxidase levels independently predict endothelial dysfunction in humans," Circulation, 110, 1134-9 (2004).
Wang et al., "Abstract 808: Myeloperoxidase Catalyzed protein carbamylation: A mechanism linking smoking, inflammation and atherogenesis," Circulation, 2006: American Heart Association, Inc.
Wang, et al., "Myeloperoxidase catalyzed protein carbamylation: A mechanism linking smoking, inflammation and atherogenesis," Circulation, vol. 114, No. 18, suppl S, pp. 141-142 (2006).
Wang et al., "Protein carbamylation links inflammation, smoking, uremia and atherogenesis," Nature Medicine, 13, pp. 1176-1184 (2007).
Wever et al., "The peroxidation of thiocyanate catalysed by myeloperoxidase and lactoperoxidase," Biochim Biophys Acta, 709, 212-9 (1982).
Wu et al.,T"he refined structure of nascent HDL reveals a key functional domain for particle maturation and dysfunction," Nature Structural & Molecular Biology, 14, 861-8 (2007).
Yang et al., "A novel model of inflammatory neointima formation reveals a potential role of myeloperoxidase in neointimal hyperplasia," Am J Physiol Heart Circ Physiol, 291, H3087-93 (2006).
Ye et al., "Antibodies that recognize nitrotyrosine", Methods Enzymol, 269, 201-209 (1996).
Zhang et al., "Association between myeloperoxidase levels and risk of coronary artery disease," JAMA, 286, 2136-42 (2001).
Zhang et al., "Myeloperoxidase functions as a major enzymatic catalyst for initiation of lipid peroxidation at sites of inflammafion," J Biol Chem, 277, 46116-22 (2002).
Zheng et al., "Apolipoprotein A-I is a selective target for myeloperoxidase-catalyzed oxidation and functional impairment in subjects with cardiovascular disease," J Clin Invest, 114, 529-41 (2004).
Zheng et al., "Localization of nitration and chlorination sites on apolipoprotein A-I catalyzed by myeloperoxidase in human atheroma and associated oxidative impairment in ABCA1-dependent cholesterol efflux from macrophages," J Biol Chem, 280, 38-47 (2005).
webpages from http://www.prnewswire.com/cgi-gin/stories.pl?ACCT=104&STORY=/www/story/09-10-2007/0004659755..., "Cleveland Clinic-Led Research Uncovers New Mechanism that Heightens Risk of Heart Disease", Findings Appear in Sep. 9 Issue of the Journal Nature Medicine, 2 pgs. printed Sep. 10, 2007.

* cited by examiner

CARBAMYLATED PROTEINS AND RISK OF CARDIOVASCULAR DISEASE

STATEMENT OF GOVERNMENT SUPPORT

The work described in this application was supported, at least in part, by National Institutes of Health grants HL70621, HL076491, and HL077107. The US. Government has certain rights in this invention.

PRIORITY CLAIM

This application is a national phase application of, claims priority to, and any other benefit, International Application No. PCT/US2008/074557, filed on Aug. 28, 2008, and entitled CARBAMYLATED PROTEINS AND RISK OF CARDIOVASCULAR DISEASE, which claims priority to, and any other benefit of U.S. Provisional Application No. 60/968,688, filed on Aug. 29, 2007; U.S. Provisional Application No. 60/967,431, filed on Sep. 5, 2007; and U.S. Provisional Application No. 60/970,641, filed on Sep. 7, 2007, all of which are incorporated by reference herein in their entirety.

FIELD OF THE INVENTION

The present invention relates to the field of cardiovascular disease. More specifically, it relates to markers and methods for determining whether a subject, particularly a human subject, is at risk of developing cardiovascular disease, having cardiovascular disease, or experiencing a complication of cardiovascular disease near term (e.g., within 3 years). The present application also relates to the use of such markers to evaluate therapeutic agents.

BACKGROUND

Cardiovascular disease (CVD) is the general term for heart and blood vessel diseases, including atherosclerosis, coronary heart disease, cerebrovascular disease, aorto-iliac disease, and peripheral vascular disease. Subjects with CVD may develop a number of complications, including, but not limited to, myocardial infarction, stroke, angina pectoris, transient ischemic attacks, congestive heart failure, aortic aneurysm and death. CVD accounts for one in every two deaths in the United States and is the number one killer disease. Thus, prevention of cardiovascular disease is an area of major public health importance.

A low-fat diet and exercise are recommended to prevent CVD. In addition, a number of therapeutic agents may be prescribed by medical professionals to those individuals who are known to be at risk for developing or having CVD. These include lipid-lowering agents that reduce blood levels of cholesterol and trigylcerides, agents that normalize blood pressure, agents, such as aspirin or platelet ADP receptor antagonist (e.g., clopidogrel and ticlopidine) that prevent activation of platelets and decrease vascular inflammation, and pleotrophic agents such as peroxisome proliferator activated receptor (PPAR) agonists, with broad-ranging metabolic effects that reduce inflammation, promote insulin sensitization, improve vascular function, and correct lipid abnormalities. More aggressive therapy, such as administration of multiple medications or surgical intervention may be used in those individuals who are at high risk. Since CVD therapies may have adverse side effects, it is desirable to have methods for identifying those individuals who are at risk, particularly those individuals who are at high risk, of developing or having CVD and/or experiencing a complication of cardiovascular disease/major adverse cardiac event near term, e.g., within three years or six months.

SUMMARY OF THE INVENTION

The present invention provides methods for characterizing a subject's, particularly a human subject's, risk of having cardiovascular disease or developing cardiovascular disease. Also provided are methods for characterizing a subject's risk of experiencing a complication of cardiovascular disease near term, i.e., within 3 years, 6 months, or 1 month, and methods for determining whether a subject presenting with chest pain is at risk of experiencing a heart attack or other major adverse cardiac event within 6 months of presenting with chest pain or suspected acute coronary syndrome. The present methods are especially useful for identifying those subjects who are in need of highly aggressive CVD therapies as well as those subjects who require no therapies targeted at inhibiting or preventing CVD or complications of CVD.

The present methods involve determining levels of certain homocitrulline-containing biomarkers (referred to hereinafter collectively as "carbamylated biomarkers") in a bodily fluid of the test subject and/or comparing the levels of the carbamylated biomarker to a control value. In one embodiment, the present methods comprise determining levels of carbamylated albumin, carbamylated apolipoprotein A, carbamylated fibrinogen and/or carbamylated immuoglobulin (IgG) in the blood, serum, or plasma of a test subject and/or comparing these levels with a control or representative value that is based on the levels of said select carbamylated protein in the blood, serum or plasma of a reference cohort, e.g. a population of apparently healthy control subjects or a population of control subjects who have not experienced a major adverse cardiac event. In another embodiment, the present methods comprise determining levels of total carbamylated protein (also known as total protein-bound homocitrulline) in the serum or plasma of a test subject and/or comparing such levels with a control value that is based on levels of total carbamylated protein in the serum or plasma of a population of control subjects. In another embodiment, the methods comprise determining levels of free homocitrulline in the blood, serum, plasma, saliva, or urine of a test subject and/or comparing such levels with a control value based on levels of free homocitrulline in comparable bodily fluids obtained from a population of control subjects.

In certain embodiments the test subject is a smoker. In certain embodiments, the test subject is a non-smoker. In certain embodiments, the test subject has normal renal function. In certain embodiments, the test subject does not have normal renal function, e.g., the subject has chronic kidney disease. In certain embodiments, the test subject is a diabetic. In certain embodiments, the test subject is non-diabetic. In certain embodiments, the control subjects are members of the general population. In certain embodiments, the test subject and/or control subjects lacks symptoms of cardiovascular disease. In certain embodiments, the test subject and/or control subjects lack clinical evidence of cardiovascular disease. In certain embodiments, the control subjects are matched to the test subject, e.g. the test subject and control subjects are in the same age bracket, are the same gender, etc.

In one embodiment, the method which involves determining levels of certain carbamylated proteins in a bodily fluid of the test subject and/or comparing these levels with a control or reference value characterizes the subject's present risk of having CVD, as determined using standard protocols for diagnosing CVD. Moreover, the extent of the difference between the test subject's select carbamylated protein levels the control value is also useful for characterizing the extent of the risk and thereby, determining which subjects would most greatly benefit from certain therapies. In another embodiment, the method which involves determining levels of certain carbamylated proteins in a bodily fluid of the test subject and/or comparing these levels with a control or reference value comparison characterizes the subject's risk of developing CVD in the future. In another embodiment, the methods which involve determining levels of total carbamylated protein, select carbamylated protein, and/or total free homocitrulline in the subject's bodily fluid can be used to characterize the subject's risk of experiencing a complication of CVD (or major adverse cardiac event) within the subsequent three years. Examples of such complications include, but are not limited myocardial infarction, heart failure, and impaired left ventricular systolic function (cardiac ejection fraction less than normal).

The present methods can also be used to determine if a subject presenting with chest pain or suspected acute coronary syndrome is at risk of experiencing a major adverse cardiac event, such as a myocardial infarction, reinfarction, the need for revascularization, or death, near term, e.g., within the following day, one month, 3 months or 6 months after the subject presents with chest pain.

In another embodiment, the methods which involve determining levels of certain carbamylated proteins in a bodily fluid of the test subject and/or comparing these levels with a control or reference value can be used to monitor the status (e.g. progression or regression) of CVD in a subject over time. In one embodiment, the method comprises determining the blood, plasma, or serum levels of one or more of the select carbamylated proteins in a test sample taken from the subject at an initial time and in a corresponding test sample taken from the subject at a subsequent time. An increase in levels of the select carbamylated proteins in the blood, serum, or plasma taken at the subsequent time as compared to the initial time indicates that a subject's risk of having CVD has increased. A decrease in levels of the select carbamylated protein indicates that the subject's risk of having CVD has decreased. For those subjects who have already experienced an acute adverse cardiovascular event such as a myocardial infarction or ischemic stroke, such methods are also useful for assessing the subject's risk of experiencing a subsequent acute adverse cardiovascular event. In such subjects, an increase in levels of carbamylation markers indicates that the subject is at increased risk of experiencing a subsequent adverse cardiovascular event. A decrease in levels of the carbamylation biomarkers in the subject over time indicates that the subject's risk of experiencing a subsequent adverse cardiovascular event has decreased.

In another embodiment, the methods which involve determining levels of certain select carbamylated proteins in a bodily fluid of the test subject can be used to evaluate the effect of a therapeutic agent on a subject with a disease associated with inflammation or oxidation, e.g. cardiovascular disease or asthma. In one embodiment, the method comprises comparing levels of one or more of the select carbamylated proteins in a biological sample taken from the subject prior to therapy with levels of the one or more carbamylated proteins in a corresponding biological sample taken from the subject during or following therapy. A decrease in levels of the one or more carbamylated proteins in the sample taken after or during therapy as compared to levels of the one or more carbamylated proteins in the sample taken before therapy is indicative of a positive effect of the therapy on the disease in the treated subject.

DETAILED DESCRIPTION OF THE INVENTION

Figure 1:
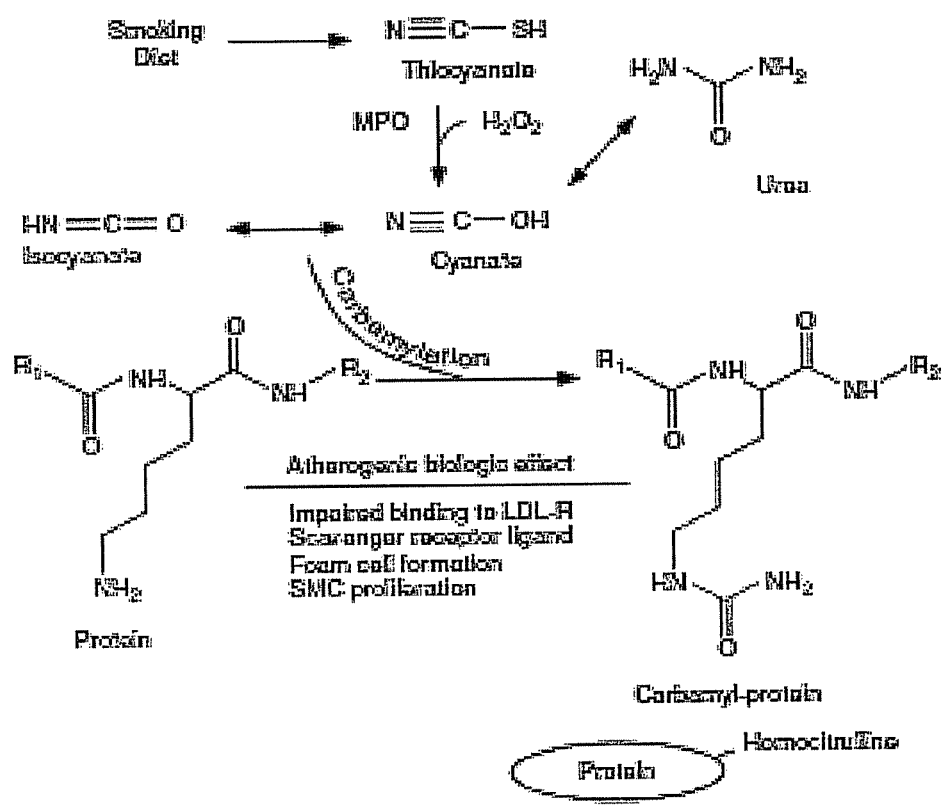
FIG. 1 is a schematic illustration of pathways for promoting protein carbamylation and their link to atherosclerosis. Diet and smoking are major determinants of plasma thiocyanate ($SCN^-$) levels. Leukocyte myeloperoxidase (MPO) uses $H_2O_2$ and $SCN^-$ as co-substrates to generate $OCN^-$ and promote protein carbamylation at sites of inflammation such as atherosclerotic plaque. Protein carbamylation is also promoted during renal disease and uremia via the equilibrium that exists between urea and $OCN^-$.

The present invention will now be described by reference to more detailed embodiments, with occasional reference to the accompanying drawings. This invention may, however, be embodied in different forms and should not be construed as limited to the embodiments set forth herein. Rather these embodiments are provided so that this disclosure will be thorough and complete, and will convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values; however, inherently contain certain errors necessarily resulting from error found in their respective measurements.

All publications, patent applications, patents, and other references mentioned herein are incorporated by reference in their entirety.

Methods and Markers for Predicting Risk of Cardiovascular Disease

Provided herein are methods and markers for characterizing a subject's risk for developing CVD, having CVD. In certain embodiments, the methods and markers can also be used to characterize a subject's risk of experiencing a major adverse cardiac event or a complication of cardiovascular disease within the ensuing 3 years, 1 year, 6 months, or month. As used herein the term "Major Adverse Cardiac Event" or "MAC" refers to myocardial infarction, stroke, need for revascularization, and death. As used herein the term "Complication of Cardiovascular Disease" refers to: myocardial infarction, stroke, angina pectoris, transient ischemic attacks, congestive heart failure, aortic aneurysm, need for revascularization, having an abnormal coronary angiogram, having an abnormal stress test, or having an abnormal cardiac perfusion study. Such methods and markers are useful for characterizing a subject's risk of having vulnerable plaque.

In certain embodiments, such methods involve determining levels of one or more select carbamylated serum/plasma proteins in the blood, serum, or plasma of the test subject and/or comparing these levels to a control value that is derived from levels of the one or more carbamylated proteins in comparable bodily samples of a reference cohort or population of control subjects. The select carbamylated proteins include certain plasma/serum proteins other than apolipoprotein B, the protein component of LDL. Preferably the select carbamylated protein is albumin, fibrinogen, immunoglobulin, or apolipoprotein A. Test subjects whose levels of the one or more select carbamylated proteins are above the control value or in the higher range of control values are at greater risk of having or developing cardiovascular disease than test subjects whose levels of the one more select carbamylated proteins are at or below the control value or in the lower range of control values. Moreover, the extent of the difference between the subject's carbamylated protein levels and the control value is also useful for characterizing the extent of the risk and thereby, determining which subjects would most greatly benefit from certain therapies. In another embodiment, the select carbamylated proteins can be used to monitor progression of CVD in a subject with CVD. In another embodiment, the select carbamylated proteins can be used to evaluate the effect of therapeutic agents on a subject with a disease associated with inflammation or oxidation, such as CVD or asthma.

In certain embodiments, the methods for identifying subjects who are at risk of experiencing a complication of cardiovascular disease near term (i.e., within the ensuing 3 years, 1 year, 6 months or 1 month) comprise determining the levels of total protein or peptide bound homocitrulline in the serum, plasma, or blood of a test subject, and/or comparing these levels to a reference value. In certain embodiments the methods for identifying subjects who are at risk of experiencing a complication of cardiovascular disease near term comprise determining the levels of free homocitrulline in the serum, plasma, blood, saliva, or urine of a test subject and/or comparing these levels to a reference value. Test subjects who have elevated levels of total protein bound homocitrulline or free homocitrulline in the aforementioned bodily fluids as compared to a reference value that is based on the levels of total protein-bound and/or free homocitrulline in comparable bodily fluids from a cohort of control subjects are at greater risk of experiencing a complication of CVD near term than test subjects whose levels of total carbamylated serum or plasma proteins and/or levels of free homocitrulline are at or below the reference value.

In certain embodiments, the subject's risk profile for CVD is determined by combining a first risk value, which is obtained by comparing levels of one or more carbamylated biomarkers in a bodily sample of the subject with levels of said one or more carbamylated biomarkers in a control population, with one or more additional risk values to provide a final risk value. Such additional risk values may be obtained by procedures including, but not limited to, determining the subject's blood pressure, assessing the subject's response to a stress test, determining levels of myeloperoxidase, C-reactive protein, low density lipoprotein, or cholesterol in a bodily sample from the subject, or assessing the subject's atherosclerotic plaque burden.

In one embodiment, the method is used to assess the test subject's risk of having cardiovascular disease. Medical procedures for determining whether a human subject has coronary artery disease or is at risk for experiencing a complication of coronary artery disease include, but are not limited to, coronary angiography, coronary intravascular ultrasound (IVUS), stress testing (with and without imaging), assessment of carotid intimal medial thickening, carotid ultrasound studies with or without implementation of techniques of virtual histology, coronary artery electron beam computer tomography (EBTC), cardiac computerized tomography (CT) scan, CT angiography, cardiac magnetic resonance imaging (MRI), and magnetic resonance angiography (MRA.). Because cardiovascular disease, typically, is not limited to one region of a subject's vasculature, a subject who is diagnosed as having or being at risk of having coronary artery disease is also considered at risk of developing or having other forms of CVD such as cerebrovascular disease, aortic-iliac disease, and peripheral artery disease. Subjects who are at risk of having cardiovascular disease are at risk of having an abnormal stress test or abnormal cardiac catherization. Subjects who are at risk of having CVD are also at risk of exhibiting increased carotid intimal medial thickness and coronary calcification, characteristics that can be assessed using non-invasive imaging techniques. Subjects who are at risk of having CVD are also at risk of having an increased atheroscleorotic plaque burden, a characteristic that can be examined using intravascular ultrasound.

In another embodiment, the present methods are used to assess the test subject's risk of developing cardiovascular disease in the future. In another embodiment, the present methods are used to determine if a subject presenting with chest pain or suspected acute coronary syndrome is at risk of experiencing a heart attack or other major adverse cardiac event, such as a heart attack, a myocardial infarction, reinfarction, the need for revascularization, or death, within the following day, 3 months, or 6 months after presenting with chest pain.

Biological Samples

Suitable biological. samples useful for predicting or monitoring cardiovascular disease in a subject or for assessing the effect of therapeutic agents on subjects with a disease associated with inflammation and oxidation, e.g. cardiovascular disease, include but are not limited to whole blood samples, samples of blood fractions, including but not limited to serum and plasma. The sample may be fresh blood or stored blood (e.g. in a blood bank) or blood fractions. The sample may be a blood sample expressly obtained for the assays of this invention or a blood sample obtained for another purpose which can be subsampled for the assays of this invention. The sample may or may not include apolipoprotein B.

Whole blood may be obtained from the subject using standard clinical procedures. In another embodiment, the biological sample is plasma. Plasma may be obtained from whole blood samples by centrifugation of anti-coagulated blood. Such process provides a buffy coat of white cell components and a supernatant of the plasma. In another embodiment, the biological sample is serum. Serum may be obtained by centrifugation of whole blood samples that have been collected in tubes that are free of anti-coagulant. The blood is permitted to clot prior to centrifugation. The yellowish-reddish fluid that is obtained by centrifugation is the serum.

The sample may be pretreated as necessary by dilution in an appropriate buffer solution, heparinized, concentrated if desired, or fractionated by any number of methods including but not limited to ultracentrifugation, fractionation by fast performance liquid chromatography (FPLC), or precipitation of apolipoprotein B containing proteins with dextran sulfate or other methods. Any of a number of standard aqueous buffer solutions, employing one of a variety of buffers, such as phosphate, Tris, or the like, at physiological pH can be used.

Test Subjects

The subject is any human or other animal to be tested for characterizing its risk of having CVD, developing CVD, experiencing a complication of CVD near term, or experiencing a second vascular event. In certain embodiments, the subject does not otherwise have an elevated risk of an adverse cardiovascular event. Subjects having an elevated risk of an adverse cardiovascular event include those with a family history of cardiovascular disease, elevated lipids, smokers, prior acute cardiovascular event, etc. (See, e.g., Harrison's Principles of Experimental Medicine, 15th Edition, McGraw-Hill, Inc., N.Y.—hereinafter "Harrison's").

In certain embodiments the subject has no signs or symptoms of CVD, e.g. angina pectoris. In certain embodiments, the subject has chest pain. In certain embodiments, the subject has no clinical evidence of cardiovascular disease. For example, such subjects have no history of myocardial infarction, stroke, revascularization, transient ischemic attack, or no significant abnormalities on cardiac catheterization (coronary angiography), myocardial perfusion, or stress test.

In certain embodiments the test subject is a non-smoker. "Nonsmoker" means an individual who, at the time of the evaluation, is not a smoker. This includes individuals who have never smoked as well as individuals who in the past have smoked but have not used tobacco products within the past year. In certain embodiments the test subject is a smoker.

In certain embodiments, the test subject has normal renal function. Renal function can be assessed by standard methods, for example by determining the subject serum creatinine levels or blood urea nitrogen levels. In certain embodiments, the subject does not have normal renal function, e.g. the test subject has chronic kidney disease. In certain embodiments, the test subject is a diabetic. In certain embodiments, the test subject is non-diabetic.

Immunoassays for Determining Levels of Protein Bound Homocitrulline or Free Homocitrulline Levels of total protein bound homocitrulline, select protein (e.g. immunoglobulin, apolipoprotein A, fibrinogen, or albumin) bound homocitrulline and/or free homocitrulline in the biological sample can be determined using polyclonal or monoclonal antibodies that are immunoreactive with such carbamylated biomarkers. Such antibodies may include, but are not limited to, polyclonal, monoclonal, chimeric, single chain, and Fab fragments. In those embodiments where the biomarker is a select carbamylated protein such as carbamylated fibrinogen, carbamylated albumin, carbamylated immunoglobulin or carbamylated apolipoprotein A, the assay may be a dual immunoassay which employ an antibody that is immunoreactive, more preferably immunospecific, with the select plasma/serum protein and an antibody that is immunoreactive, preferably immunospecific, with homocitrulline bound peptides or free homocitrulline. The term "immunospecific" means the antibodies have substantially greater affinity for the homocitrulline, either peptide bound or free, than for peptide-bound homocitrulline or lysine. In other words, the method may involve immunoprecipitating one of the select plasma/serum proteins from the test sample, and then determining the levels of homocitrulline in the immunoprecipitated molecule using an anti-homocitrulline antibody. Alternatively, the method may employ an antibody which reacts with, or preferably is immunospecific, for a homocitrulline-containing form of the select plasma protein that is being assayed Suitable immunoassays include, by way of example, radioimmunoassays, both solid and liquid phase, fluorescence-linked assays, competitive immunoassays, or enzyme-linked immunosorbent assays. In certain embodiments, the immunoassays are also used to quantify the amount of the carbamylated biomarker that is present in the sample.

Various immunoassays may be used for screening to identify antibodies having the desired specificity. These include protocols that involve competitive binding or immunoradiometric assays and typically involve the measurement of complex formation between the respective carbamylated protein and the antibody.

The method comprises contacting a sample taken from the individual with one or more of the present antibodies; and assaying for the formation of a complex between the antibody and a protein or peptide in the sample. For ease of detection, the antibody can be attached to a substrate such as a column, plastic dish, matrix, or membrane, preferably nitrocellulose. The sample may be a tissue or a biological fluid, including urine, whole blood, or exudate, preferably serum. The sample may be untreated, subjected to precipitation, fractionation, separation, or purification before combining with the antibody. Interactions between antibodies in the sample and the carbamylated biomarker are detected by radiometric, colorimetric, or fluorometric means, size-separation, or precipitation. Preferably, detection of the antibody-protein or peptide complex is by addition of a secondary antibody that is coupled to a detectable tag, such as for example, an enzyme, fluorophore, or chromophore. Formation of the complex is indicative of the presence of carbamylated biomarker in the individual's biological sample.

In certain embodiments, the method employs an enzyme-linked immunosorbent assay (ELISA) or a Western immuno-blot procedure.

Preparation of Antibodies

Monoclonal antibodies are produced according to established procedures. Generally, homocitrulline containing peptide fragments are used to immunize a host animal. Suitable host animals, include, but are not limited to, rabbits, mice, rats, goats, and guinea pigs. Various adjuvants may be used to increase the immunological response in the host animal. The adjuvant used depends, at least in part, on the host species. Such animals produce heterogenous populations of antibody molecules, which are referred to as polyclonal antibodies and which may be derived from the sera of the immunized animals.

For preparation of monoclonal antibodies, conventional hybridoma techniques are used. Such antibodies are produced by continuous cell lines in culture. Suitable techniques for preparing monoclonal antibodies include, but are not limited to, the hybridoma technique, the human B-cell hybridoma technique, and the EBV hybridoma technique.

Monoclonal antibodies, which are homogenous populations of an antibody that bind to a particular antigen, are obtained from continuous cells lines. Conventional techniques for producing monoclonal antibodies are the hybridoma technique of Kohler and Millstein (Nature 356:495-497 (1975)) and the human B-cell hybridoma technique of Kosbor et al (Immunology Today 4:72 (1983)). Such antibodies may be of any immunoglobulin class including IgG, IgM, IgE, Iga, IgD and any class thereof. Procedures for preparing antibodies against modified amino acids, such as for example, 3-nitrotyrosine are described in Ye, Y. Z., M. Strong, Z. Q. Huang, and J. S. Beckman. 1996. Antibodies that recognize nitrotyrosine. Methods Enzymol. 269:201-209.

Polyclonal antibodies are generated using conventional techniques by administering the immunogen, i.e., the homocitrulline containing peptide or the serum protein, to a host animal. Depending on the host species, various adjuvants may be used to increase immunological response. Among adjuvants used in humans, Bacilli-Calmette-Guerin (BCG), and *Corynebacterium parvum*, are especially preferable. Conventional protocols are also used to collect blood from the immunized animals and to isolate the serum and or the IgG fraction from the blood.

Additional Methods for Measuring of Carbamylated Biomarkers

Mass spectrometry-based methods (e.g. LC/ESI/MS/MS) may also be used to assess levels of total carbamylated proteins or free homocitrulline in the biological sample as shown in the examples below. Such methods are standard in the art and include, for example, HPLC with on-line electrospray ionization tandem mass spectometry. Synthetic standard tryptic digets peptides for parent (unmodifed) and modified (nitrated, chlorinated) forms can be made readily with automated peptide synthesizers using commercially available fmoc modified amino acids. The parent molecules i.e., the proteins or amino acids that are not carbamylated will have different masses than the carbamylated molecules). Thus, distinct parent.fwdarw.daughter ion transitions for each peptide would be achievable.

Control Value

Levels of the carbamylated biomarker in the biological sample obtained from the test subject may compared to a control value. The control value is based upon levels of the carbamylated biomarker in comparable samples obtained from a reference cohort, e.g., the general population or a select population of human subjects.

The select population may be comprised of smokers, non-smokers diabetics, non-diabetics, those with normal renal function or those with abnormal renal function. The select population may be comprised of apparently healthy subjects. "Apparently healthy", as used herein, means individuals who have not previously had any signs or symptoms indicating the presence of atherosclerosis, such as angina pectoris, history of an acute adverse cardiovascular event such as a myocardial infarction or stroke, evidence of atherosclerosis by diagnostic imaging methods including, but not limited to coronary angiography. Apparently healthy individuals also do not otherwise exhibit symptoms of disease. In other words, such individuals, if examined by a medical professional, would be characterized as healthy and free of symptoms of disease. In another example, the control value can be derived from an apparently healthy nonsmoker population. "Nonsmoker", as used herein, means an individual who, at the time of the evaluation, is not a smoker. This includes individuals who have never smoked as well as individuals who in the past have smoked but have not used tobacco products within the past year. An apparently healthy, nonsmoker population may have a different normal range of carbamylated biomarker than will a smoking population or a population whose member have had a prior cardiovascular disorder. Accordingly, the control values selected may take into account the category into which the test subject falls. Appropriate categories can be selected with no more than routine experimentation by those of ordinary skill in the art.

The control value is related to the value used to characterize the level of the carbamylated biomarker from the test subject. Thus, if the level of the carbamylated biomarker is an absolute value such as the units of a select carbamylated protein per ml of blood, the control value is also based upon the units of the select carbamylated protein per ml of blood in individuals in the general population or a select population of human subjects.

The control value can take a variety of forms. The control value can be a single cut-off value, such as a median or mean. The control value can be established based upon comparative groups such as where the risk in one defined group is double the risk in another defined group. The control values can be divided equally (or unequally) into groups, such as a low risk group, a medium risk group and a high-risk group, or into quadrants, the lowest quadrant being individuals with the lowest risk the highest quadrant being individuals with the highest risk, and the test subject's risk of having CVD can be based upon which group his or her test value falls.

Control values of carbamylated biomarkers in biological samples obtained, such as for example, mean levels, median levels, or "cut-off" levels, are established by assaying a large sample of individuals in the general population or the select population and using a statistical model such as the predictive value method for selecting a positivity criterion or receiver operator characteristic curve that defines optimum specificity (highest true negative rate) and sensitivity (highest true positive rate) as described in Knapp, R. G., and Miller, M. C. (1992). Clinical Epidemiology and Biostatistics. William and Wilkins, Harual Publishing Co. Malvern, Pa., which is specifically incorporated herein by reference. A "cutoff" value can be determined for each risk predictor that is assayed.

Comparison of The Carbamylated Biomarker from the Test Subject to the Control Value Levels of the carbamylated biomarker, e.g., the select carbamylated protein, in the individual's biological sample may be compared to or correlated with a single control value or to a range of control values. If the level of the select carbamylated protein in the test subject's biological sample is greater than the control value or exceeds or is in the upper range of control values, the test subject is at greater risk of developing or having CVD than individuals with levels comparable to or below the control value or in the lower range of control values. In contrast, if levels of the select carbamylated protein in the test subject's biological sample is below the control value or is in the lower range of control values, the test subject is at a lower risk of developing or having CVD than individuals whose levels are comparable to or above the control value or exceeding or in the upper range of control values. The extent of the difference between the test subject's risk predictor levels and control value is also useful for characterizing the extent of the risk and thereby, determining which individuals would most greatly benefit from certain aggressive therapies. In those cases, where the control value ranges are divided into a plurality of groups, such as the control value ranges for individuals at high risk, average risk, and low risk, the comparison involves determining into which group the test subject's level of the relevant risk predictor falls.

The present predictive tests are useful for determining if and when therapeutic agents that are targeted at preventing CVD or for slowing the progression of CVD should and should not be prescribed for a individual. For example, individuals with values of carbamylated biomarkers, e.g., select carbamylated protein, above a certain cutoff value, or that are in the higher tertile or quartile of a "normal range," could be identified as those in need of more aggressive intervention with lipid lowering agents, life style changes, etc.

Evaluation of Therapeutic Agents

Also provided are methods for evaluating the effect of therapeutic agents for diseases associated with inflammation or oxidation, e.g. CVD or asthma, on individuals who have been diagnosed as having or as being at risk of developing such diseases. Such therapeutic agents include, but are not limited to, anti-inflammatory agents, insulin sensitizing agents, antihypertensive agents, anti-thrombotic agents, anti-platelet agents, fibrinolytic agents, lipid reducing agents, direct thrombin inhibitors, ACAT inhibitor, CDTP inhibitor thioglytizone, glycoprotein IIb/IIIa receptor inhibitors, agents directed at raising or altering HDL metabolism such as apoA-I milano or CETP inhibitors (e.g., torcetrapib), or agents designed to act as artificial HDL. Such evaluation comprises determining the levels of one or more select carbamylated protein in a biological sample taken from the subject prior to administration of the therapeutic agent and a corresponding biological fluid taken from the subject following administration of the therapeutic agent. A decrease in the level of the select carbamylated protein(s) in the sample taken after administration of the therapeutic as compared to the level of the select carbamylated protein(s) in the sample can also be used to monitor anti-inflammatory and/or antioxidant actions of therapeutic agents. Therapeutic agents that can be monitored in accordance with an aspect of the invention can include any pharmacodynamic agent that exhibits an anti-inflammation and/or antioxidant action in vivo through suppression of multiple distinct oxidation pathways used in the formation of myeloperoxidase derived carbamylated proteins. These anti-inflammation and/or antioxidant actions can be systemic and can be monitored by monitoring the systemic levels of select carbamylated proteins in a subject before and after administration of the therapeutic agent.

An example of a therapeutic agent for which the anti-inflammation and/or antioxidant action can be monitored in accordance with an aspect of the invention is an HMG CoA reductase inhibitor (3-hydroxymethylglutaryl coenzyme A reductase inhibitors)(i.e., statin). HMG-CoA (3-hydroxy methylglutaryl coenzyme A) reductase is the microsomal enzyme that catalyzes the rate limiting reaction in cholesterol biosynthesis (HMG-CoA Mevalonate). Statins inhibit HMG-CoA reductase, and as a result inhibit the synthesis of cholesterol. It is believed that these anti-inflammatory and antioxidant actions likely result from inhibition of isoprenylation of Rac and Rho. Rac is a key component of the NAD(P)H oxidase complex of both leukocytes and vascular cells. It is further believed that statin induced inhibition of Rac isoprenylation prevents its translocation to the plasma membrane, leading to suppression in superoxide formation from cells. Rho is a small GTPase involved in cell signaling. It is believed that inhibition of Rho isoprenylation results in enhanced nitric oxide production from endothelial cells, which is likely to produce an overall antioxidant action.

EXAMPLES

The following examples are included for purposes of illustration and are not intended to limit the scope of the invention.

Example 1

Elevated Levels of Protein Bound Homocitrulline as an Independent Biomarker for CVD in Non-Uremic Patients and as a Risk Predictor for Near Term Complications of CVD In this study we provide biochemical, animal model and clinical data supporting a role for myeloperoxidase(MPO)-catalyzed oxidation of thiocyanate ($SCN^-$), an abundant anion in plasma that is increased in smokers, as a novel and quantitatively dominant mechanism for inducing protein carbamylation in vivo, and during development of atherosclerosis in humans (FIG. 1).

A potential role for carbamylation in post-translational modification of proteins during human health and disease has thus far been solely attributed to uremia[1-4]. One of the earliest post-translational modifications of proteins elucidated, carbamylation was identified as an untoward side effect during reversible denaturation-renaturation studies of proteins with urea, where changes in protein molecular weight and isoelectric point, accompanied by enzymatic activity loss, were noted[5,6]. Urea is in equilibrium with trace levels of the electrophilic species cyanate ($OCN^-$) (FIG. 1), which can react with nucleophilic groups on proteins through carbamylation[5,7]. Accordingly, a role for protein carbamylation in end stage renal disease has been hypothesized to participate in the "toxemia of uremia"[1-4,8-11]. Because of the extremely low yield of protein carbamylation under normal plasma levels of urea, the potential involvement of this pathway in the absence of renal disease has not been explored.

MPO is an abundant heme protein in neutrophils, monocytes and certain tissue macrophages, such as those found in human atheroma. Mechanisms linking MPO to CAD have primarily revolved around MPO-catalyzed oxidation reactions that either result in catalytic consumption of nitric oxide with consequent endothelial dysfunction[20-23], or generation of reactive halogenating and nitrating species capable of rendering LDL atherogenic[14] and high density lipoprotein (HDL) dysfunctional[24-27]. Interestingly, none of these reactions involve thiocyanate ($SCN^-$), a pseudohalide that serves as a preferred substrate for MPO[28]. $SCN^-$ levels vary in plasma depending upon dietary intake (FIG. 1), with normal plasma levels in non-smokers being in the range of 20-100 $\mu M$[29]. Plasma levels of $SCN^-$ in smokers are substantially higher[30].

At plasma levels of halides and $SCN^-$, it is estimated that oxidation of $SCN^-$ can account for approximately 50% of the $H_2O_2$ consumed by MPO[31]. The major product formed is hypothiocyanous acid (HOSCN), a relatively weak oxidant with bacteriostatic activity[32]. A role for heme peroxidases in catalyzing protein carbamylation during inflammation has not yet been explored. We hypothesized that MPO can utilize $SCN^-$ as co-substrate with $H_2O_2$ under physiological conditions to produce $OCN^-$ (Equation 1), and thus, potentially serve as a novel

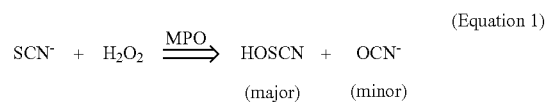

$$SCN^- + H_2O_2 \xrightarrow{MPO} \underset{\text{(major)}}{HOSCN} + \underset{\text{(minor)}}{OCN^-} \quad \text{(Equation 1)}$$

inflammation-driven mechanism heightened in smokers for promoting protein carbamylation (FIG. 1) within human atherosclerotic plaque.

Methods

Materials and General Procedures.

1,1'-dioctadecyl-3,3,3',3'-tetramethylyindocarbocyanine perchlorate (DiI) was obtained from Molecular Probes (Eugene, Oreg.). Organic solvents were obtained from Fisher Scientific Co. (Pittsburgh, Pa.). Caspase-3/7 assay kit (Lot #220150) was purchased from Promega (Madison, Wis.) and cell proliferation ELISA, BrdU (colorimetric) kit (Lot #11647229001) was from Roche (Indianapolis, Ind.). All other reagents and materials were obtained from Sigma Chemical Co. (St. Louis, Mo.) unless otherwise indicated. Protein content was determined by the Markwell-modified Lowry protein assay[44]. Human LDL and HDL were isolated from whole blood of healthy volunteers by established methods[45]. Human myeloperoxidase (MPO) (donor: hydrogen peroxide, oxidoreductase, EC 1.11.1.7), $NO_2$-LDL and AcLDL were prepared as described in Podrez et al[14].

ESI-MS Analysis of the $MPO/SCN^-/H_2O_2$ System Reaction Products.

Negative ion ESI-MS was carried out on an API 365 triple quadrupole mass spectrometer (Applied Biosystems, Foster, Calif.) with Ionics EP 10+ upgrade (Concord, Ontario, CA). The $MPO/SCN^-/H_2O_2$ system contained 30 nM MPO, 100 $\mu M$ either [$^{13}C$, $^{15}N$]$SCN^-$, [$^{13}C$]$SCN^-$ or [$^{12}C$]$SCN^-$, and 100 $\mu M$ $H_2O_2$. Reactions were carried out in chelex resin treated sodium phosphate buffer (10 mM, pH 7.0) supplemented with diethylenetriaminepentaacetic acid (DTPA, 100 $\mu M$). Following 1 hour reaction at 37° C., reaction products were analyzed by direct infusion in negative ion mode.

Protein Carbamylation In Vitro.

LDL (0.2 mg of protein/ml) or HDL (1 mg of protein/ml) in 50 mM sodium phosphate, pH 7.0, was incubated with either reagent $OCN^-$ (100 $\mu M$ as the potassium salt), or the MPO system (30 nM MPO, 100 $\mu M$ $SCN^-$, 100 $\mu M$ $H_2O_2$) at 37° C. for 8 h. Where indicated, a glucose (100 $\mu g/ml$)/glucose oxidase (20 ng/ml) system was used for $H_2O_2$ generation. Reactions were terminated by addition of 50 nM catalase, 40 $\mu M$ butylated hydroxytoluene, 100 $\mu M$ DTPA and dialysis against PBS containing 100 $\mu M$ DTPA.

Mouse Models.

All animal studies were performed using approved protocols from the Animal Research Committee of the Cleveland Clinic Foundation. Age- and sex-matched C57BL/6J MPO-knockout and wildtype mice (>99% genetic homogeneity) were used for peritonitis studies as previously described[37]. Human MPO transgenic (MPO-TG) mice used in studies carried the human −463G allele on a low density lipoprotein receptor deficient C57BL6/J background as described[38]. Mice were fed a high fat diet for 20 weeks (Harlan Teklad Laboratory; TD 88137) and both cholesterol and protein bound HCit quantified in aortic tissues by mass spectrometry.

Protein Bound Homocitrulline Analysis.

Protein bound HCit was quantified in tissues and plasma by stable isotope dilution HPLC with online tandem mass spectrometry following delipidation and desalting, and overnight protein hydrolysis with HCl. $[^{13}C_6{}^{15}N_2]$-u-Lys and $[^{13}C_6]$Arg were added prior to hydrolysis and used as internal standards to quantify lysine and homocitrulline, respectively. Following acid hydrolysate cleanup with mini solid-phase DSC-SCX extraction column (Discovery® DSC-SCX SPE tubes; 1 mL; Supelco Inc., Bellefonte, Pa., USA) analytes were resolved on a Phenyl column (4.6×250 mm, 5 µm Rexchrom Phenyl) (Regis, Morton Grove, Ill.) using a gradient generated between aqueous ammonium formate versus methanol/0.1% formic acid/5 mM ammonium formate mobile phases. Amino acids were analyzed on an API 365 triple quadrupole mass spectrometer with Ionics EP 10$^+$ upgrade (Concord, Ontario, CA) interfaced to a Cohesive Technologies Aria LX Series HPLC multiplexing system (Franklin, Mass.) using electrospray ionization in positive-ion mode with multiple reaction monitoring of parent and characteristic daughter ions specific for components monitored.

Protein Bound Homocitrulline Quantification: Sample Preparation.

Plasma (20 µl) was diluted to 0.6 ml with acidified $H_2O$ (1N HCl final), and a single phase mixture generated by addition of $CHCL_3/CH_3OH$ (0.67 ml:1.33 ml) to samples. Delipidated proteins were then precipitated and two phases generated by addition of 1 ml $CHCl_3$ followed by 1 ml $H_2O$. Samples were vortexed, kept in ice-water bath for 10 min, and then spun at 2,500 g, 4° C. for 40 minutes. Both upper and lower layers were removed by gentle decanting and the mid-layer containing denatured protein pellet was resuspended in 0.6 ml with acidified $H_2O$ (1N HCl final) and the delipidation/protein precipitation process repeated. Control studies confirmed that the above procedure resulted both in overall excellent protein recovery (>95%) and nominal remaining free HCit. Following addition of $[^{13}C_6{}^{15}N_2]$-u-Lys and $[^{13}C_6]$Arg (2 nmol each) as internal standards to quantify lysine and homocitrulline, respectively, proteins were hydrolyzed in 200 µl 6 N HCl under vacuum at 100° C. The hydrolysate was passed over a mini solid-phase DSC-SCX extraction column (Discovery® DSC-SCX SPE tubes; 1 ml; Supelco Inc., Bellefonte, Pa., USA) equilibrated with 2×1 ml 0.2 N formic acid and amino acids were eluted with 2×1 ml 70% methanol supplemented with 5% ammonia and 0.1 M ammonium formate. The amino acid solution was dried under vacuum and dissolved in 100 µL $H_2O$ for LC/MS/MS analysis.

Protein Bound Homocitrulline Quantification: Mass Spectometry Analysis.

HPLC with online electrospray ionization tandem mass spectometry (LC/ESI/MS/MS) was employed to quantify lysine, homocitrulline and their respective internal standards, in the protein hydrolysates. Calibration curves were prepared using varying lysine and homocitrulline levels and a fixed amount of stable isotope-labeled internal standards undergoing hydrolysis and DSC-SCX column extraction. Sample (10 µl) was injected onto a Phenyl column 94.6×250 mm, 5 µm Rexchrom Phenyl) (Regis, Morton Grove, Ill.) at a flow rate of 0.8 ml/min. Separation was performed using a gradient starting from 10 mM ammonium formate aqueous solution over 0.5 min, then linearly to 25% methanol containing 0.1% formic acid and 5 mM ammonium formate over 3 min, followed by this solution for 15 min. The HPLC column effluent was introduced into an API 365 triple quadrupole mass spectrometer with Ionics EP 10$^+$ upgrade (Concord, Ontario, CA) interfaced to a Cohesive Technologies Aria LX Series HPLC multiplexing system (Franklin, Mass.). Analyses were performed using electrospray ionization in positive-ion mode with multiple reaction monitoring of parent and characteristic daughter ions specific for components monitored. The transitions monitored were mass-to-charge ratio (m/z): m/z 147→84 for Lys; m/z 190→127 for HCit: m/z 155→90 for $[^{13}C_6, {}^{15}N_2]$Lys; and m/z 181→74 for $[^{13}C_6]$Arg. The internal standard $[^{13}C_6]$Arg was used for quantification as well as to calculate recovery rate of homocitrulline (which was >85% based upon separate control studies). The internal standard $[^{13}C_6, {}^{15}N_2]$Lys was used for quantification of lysine.

Preparation of Anti-Carbamyl-Protein Monoclonal Antibody.

A human Fab phage display library was generated from peripheral blood lymphocytes of four healthy donors using plasmids obtained from the laboratory of Dr. C. F. Barbas III (The Scripps Research Institute, La Jolla, Calif.)[6]. The donors gave written consent and the study was approved by the Ethical Committee of the Faculty of Medicine, University of Oulu, Finland. The human monoclonal anti-carbamyl antibody (K2-Fab) was selected from the library using carbamylated-LDL as panning antigen. Prior to panning, the carbamylated-LDL was tested to be non-oxidized using previously published monoclonal antibodies to oxidized-LDL[7]. After purification, K2-Fab demonstrated specific binding in a competition ELISA to carbamylated-LDL and carbamylated-bovine serum albumin, and not to native-LDL and native-BSA. Further characterization and control studies showed that antibody recognition is specific for carbamylated protein in general, with both OCN— and MPO—H2O2-SCN— modified proteins (LDL, bovine serum albumin, ovalbumin) being recognized, but not their non-carbamylated (native) counterparts.

Research Subjects and Clinical Laboratory Analyses.

Plasma specimens were obtained from GeneBank, a large (n=10,000) and well-characterized tissue repository with longitudinal data from sequential consenting subjects undergoing elective diagnostic left heart catheterization. All GeneBank participants gave written informed consent and the Institutional Review Board of the Cleveland Clinic Foundation approved the study protocol. The Framingham Risk Score was calculated for each subject as defined[46]. An estimate of glomerular filtration rate was calculated using the modification of diet in renal disease (MDRD) formula[47]. Atherosclerotic CVD was defined clinically as CAD, PAD, cerebral vascular disease, or angiographic evidence of CAD (>50% stenosis) in one or more major coronary arteries.

Lipoprotein profiles, glucose, high sensitivity C-reactive protein and creatinine levels were performed on an Abbott Architect model ci8200 (Chicago, Ill.). MPO levels were determined by the FDA cleared CardioMPO™ test (PrognostiX, Inc, Cleveland, Ohio). All laboratory analyses were performed in random order to avoid systemic bias and with investigators blinded to clinical outcomes.

Statistical Analysis.

Data are presented as median (first quartile—third quartile) for continuous measures and as number (percentage) for categorical measures. Comparisons of continuous measures between two independent groups were done using two-tailed Wilcoxon rank sum tests (Mann-Whitney test) due to the non-symmetrical distribution of many of the considered measures. Comparison of categorical measures between independent groups was done using $\chi^2$ tests. All observed counts in the $\chi^2$ were greater than the standard minimum of 5. Odds ratios were calculated with R, Version 2.1.0 (www.r-project.org), using logistic regression with case status as the dependent variable and indicators of membership in HCit quartiles (unadjusted results) or indicators of membership in HCit quartiles, Framingham Risk Score (includes variables of age, gender, fasting LDLc, HDLc, history of hypertension, diabetes and smoking), estimated MDRD, MPO and CRP (adjusted results) as predictor variables. Quartiles of HCit rather than HCit values were used as predictor variables to avoid functional assumptions about the relationship of HCit with odds. A completely additive model was used for estimating the odds ratios when adjusting for other risk factors. 95% confidence intervals for the odds ratios were calculated by transforming the Wald 95% confidence intervals for the corresponding logistic regression coefficient. Trend tests in frequencies across quartiles of HCit were done using Cochran-Armitage Trend tests, which are valid for case/control designs.

Results

MPO Catalyzed Oxidation of $SCN^-$ Produces $OCN^-$ and Facilitates Protein Carbamylation.

Figure 2:
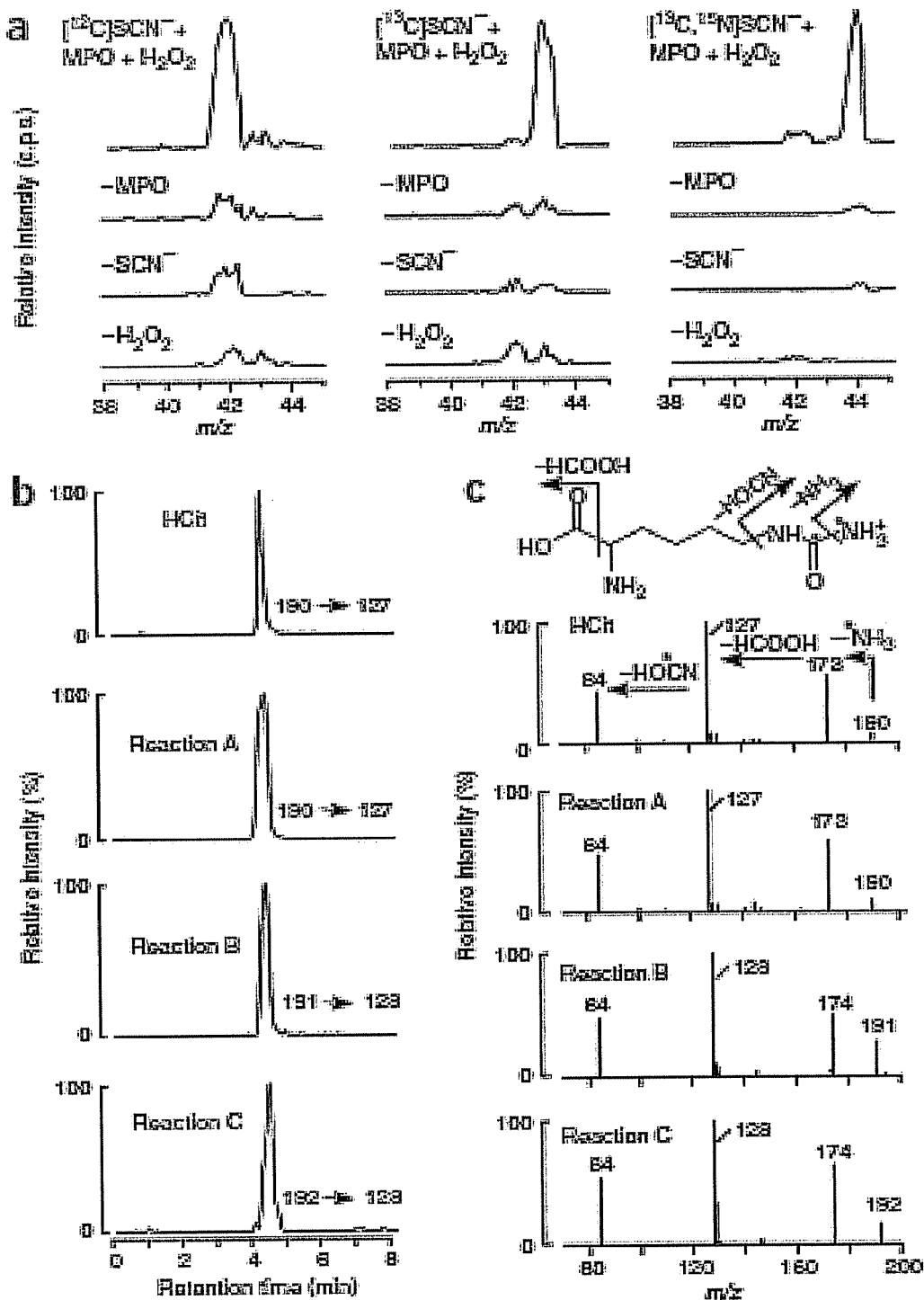
FIG. 2 shows production of $OCN^-$ and homocitrulline (HCit) in reactions of proteins with $MPO/SCN^-/H_2O_2$. (a) Direct visualization of $[^{12}C]$, $[^{13}C]$ and $[^{13}C,^{15}N]CNO^-$ formation following oxidation of the indicated isotopomers of $SCN^-$ by the $MPO/H_2O_2$ system using negative ion ESI-MS analysis. (b) Extracted ion chromatograms in positive ion multiple reaction monitoring mode of HCit standard and hydrolysates of bovine serum albumin (BSA) following reaction with (i) $MPO/[^{12}C]SCN^-/H_2O_2$, (ii) $MPO/[^{13}C]SCN^-/H_2O_2$ and (iii) $MPO/[^{13}C,^{15}N]SCN^-/H_2O_2$, with parent to daughter transitions, 190→127, 190→127, 191→128, and 192→128, respectively. (c) Collision (energy 21 eV) induced dissociation (CID) mass spectra corresponding to peaks of the HCit standard and the protein-bound HCit isotopomers produced by the $MPO/SCN^-/H_2O_2$ reaction systems (i), (ii) and (iii). Mass to charge ratio (m/z).

In initial studies, we sought to directly test the hypothesis that MPO catalyzes formation of $OCN^-$ from $SCN^-$ and $H_2O_2$ as co-substrates. Incubation of MPO with both $H_2O_2$ and natural abundance (ie. [$^{12}C$]) $SCN^-$ generated a product with appropriate mass-to-charge ratio (m/z=42) in the presence of all components of the reaction mixture, but not in the absence of any individual component (FIG. 2a). Parallel reactions mixtures using either [$^{13}C$]$SCN^-$ or [$^{13}C,^{15}N$]$SCN^-$ resulted in formation of analytes with the expected m/z of the isotopomers [$^{13}C$]$OCN^-$ (m/z=43) and [$^{13}C,^{15}n$]$OCN^-$ (m/z=44), respectively, consistent with MPO-catalyzed formation of $OCN^-$ from $SCN^-$ (FIG. 2a). Under the conditions employed, the overall yield of $OCN^-$ formation (relative to $H_2O_2$) was 8.9%.

The reaction of $OCN^-$ with nucleophilic ε-amino groups of protein lysine residues produces ε-carbamyl-lysine, also known as homocitrulline (HCit) (FIG. 1). Although the side chains of some other amino acid residues can also be carbamylated, these tend not to be stable, in contrast to carbamyl amino groups[7,34]. All N-terminal s-amino groups can be carbamylated at physiological pH[7,35]; however, carbamylation of the N-terminal amino acid seldom leads to changes in physiological function. The high abundance and relatively lower pKa value of the ε-amino lysine moiety compared with that of alternative nucleophilic targets makes lysine side chains the main amino acid target for carbamylation on proteins. To test the hypothesis that MPO catalyzed formation of $OCN^-$ facilitates protein carbamylation, we developed a stable isotope dilution mass spectrometry-based assay to quantify protein-bound HCit as a molecular marker with which to gauge the degree of protein carbamylation. When albumin was exposed to isolated human MPO in the presence of both [$^{12}C$]$SCN^-$ and $H_2O_2$, and then protein in the reaction mixture was desalted, hydrolyzed into its constituent amino acids, and monitored by HPLC with on-line tandem mass spectrometry, an analyte with the same retention time, characteristic parent→daughter ion transition, and CID spectrum (FIGS. 2b, 2c) as that of [$^{12}C$]HCit was observed. Analysis of parallel reaction mixtures exposing albumin to MPO, $H_2O_2$ and either [$^{13}C$]$SCN^-$ or [$^{13}C,^{15}N$]$SCN^-$ confirmed MPO served as an enzymatic catalyst for promoting protein carbamylation, with resultant detection of protein-bound analytes with identical retention time, characteristic parent→daughter ion transitions, and CID spectra, with that expected for generation of protein bound [$^{13}C$]HCit and [$^{13}C,^{15}N$]HCit, respectively (FIGS. 2b, 2c).

MPO Catalyzed Oxidation of $SCN^-$ Serves as a Physiological Pathway for Promoting Protein Carbamylation During Inflammation.

Figure 3:
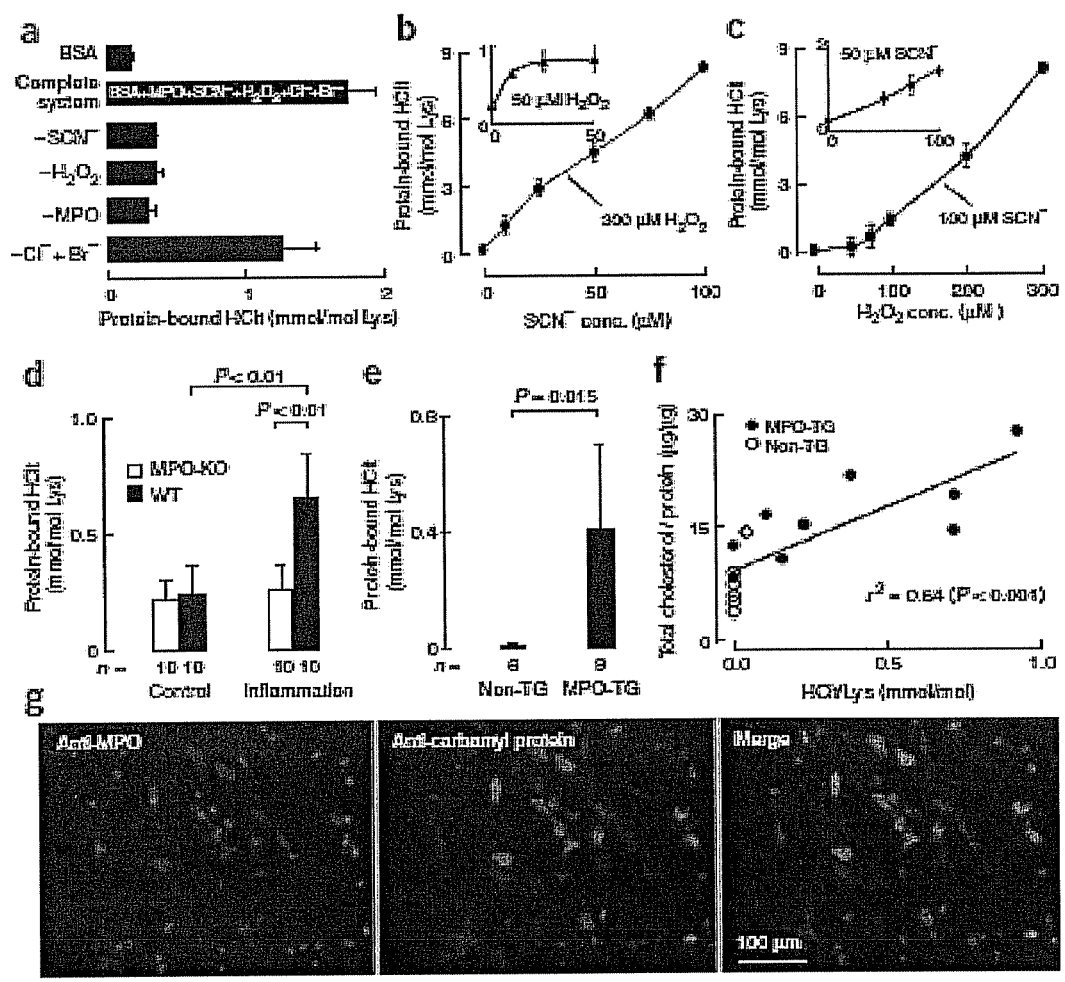
FIG. 3 shows that MPO is a catalytic source for carbamylation at sites of inflammation and within human atherosclerotic plaque. (a) Reaction requirements and quantification of protein (BSA 1 mg/mL) carbamylation by the $MPO/SCN^-/H_2O_2$ system under physiological concentrations of halides, $SCN^-$ and $H_2O_2$. Data were presented as mean±SD for 3 independent experiments. (b, c) Protein carbamylation occurs across physiological concentration ranges of $SCN^-$ and $H_2O_2$. Data are presented as mean±SD for 3 independent experiments. (d) Levels of protein bound HCit in cell pellet proteins recovered from peritoneal lavage of wild type (WT, n=10) and MPO knockout (MPO—KO, n=10) mice before (control, Ctrl) and 24 hours following induction of peritonitis (inflammation). (e) Levels of protein bound HCit and (f) relationship between total cholesterol (TC, free cholesterol+ cholesterol ester) in aorta tissue sections from $LDL-R^{-/-}$ mice (WT) and human MPO-transgenic $LDL-R^{-/-}$ mice (MPO-TG). (g) Fluorescent microscopy of human carotid atherosclerotic plaque immuno-stained with either monoclonal antibodies to (left) MPO or (center) carbamyl-proteins and (right) the merged image reveals co-localization of MPO and carbamyl-proteins, magnification 10×, nuclei were stained with DAPI.

To characterize whether protein carbamylation mediated by the MPO/$H_2O_2$/$SCN^-$ system occurs under physiologically relevant conditions, protein bound HCit was quantified in bovine serum albumin (BSA) incubated with MPO, plasma levels of both $SCN^-$ and halides (100 mM $Cl^-$ and 100 μM $Br^-$), and physiologically plausible levels of $H_2O_2$ at pH 7.0. Native BSA contains a low level of HCit, which is dramatically increased following exposure to the complete MPO/$H_2O_2$/$SCN^-$ system (FIG. 3a). Carbamylation required the presence of each component of the MPO/$H_2O_2$/$SCN^-$ system. Interestingly, the absence of the halides $Cl^-$ and $Br^-$, alternative substrates for MPO, had little effect on HCit generation, consistent with $SCN^-$ serving as a preferred substrate for MPO. Finally, quantification of protein bound HCit generation by the MPO/$H_2O_2$/$SCN^-$ system across the physiological range of $SCN^-$ and $H_2O_2$ concentrations revealed dose dependent increases in the degree of protein carbamylation (FIG. 3b,c). Collectively, these results strongly suggest that MPO may serve as a catalytic source of protein carbamylation in vivo at sites of inflammation.

To directly test whether protein carbamylation is augmented during inflammation in vivo via an MPO-driven pathway, animal model studies employing MPO knockout mice vs wildtype mice (both on C57BL/6 background) were performed. A peritonitis model of acute inflammation was used because control studies demonstrated comparable blood urea nitrogen levels between WO knockout mice vs. wildtype mice (p=0.87), and prior studies have exhaustively characterized the model, including demonstration of comparable levels of leukocyte recruitment (cell counts and differentials), protein concentration, nitric oxide synthase expression, superoxide generation, cyclooxygenase I and II expression, and lipoxygenase expression, between the MPO knockout mice vs. wildtype mice[36,37]. At baseline, comparable levels of total protein bound HCit were observed in proteins recovered in peritoneal lavage from MPO knockout mice vs. wildtype mice. With induction of peritonitis, blood urea nitrogen levels remain unchanged in wildtype and MPO knockout mice (p=0.91), yet marked increases in protein bound HCit levels were observed in both peritoneal lavage soluble and cell pellet proteins recovered from wildtype mice (FIG. 3d, data from cell pellets shown). These results are consistent with a direct and novel role of inflammation in promotion of protein carbamylation. Of interest, peritonitis-driven carbamylation was markedly attenuated in MPO knockout mice (FIG. 3d), consistent with MPO as a major catalytic source in vivo for protein carbamylation at sites of inflammation.

MPO Catalyzed Oxidation of $SCN^-$ Promotes Protein Carbamylation within Atherosclerotic Plaque in Both Human MPO Transgenic Mice and Humans.

Two independent groups have recently reported that introduction of the human MPO transgene into mice results in accelerated atherosclerosis[18,19]. We therefore examined the relationship between aortic tissue levels of protein bound HCit in human MPO transgenic versus wild type mice using an established atherosclerosis model. Both transgenic and wild type mice on the hyperlipidemic low density lipoprotein receptor null background were fed a high fat atherogenic diet for 20 weeks. Similar to prior reports[19,38], human MPO was only immunodetected in lesions in the MPO transgenic mice, with no MPO detected in aorta from the LDLR−/− mice.

Proximal aorta were harvested and then examined for total protein bound HCit and cholesterol content. A dramatic increase in protein bound HCit content was noted within the atherosclerotic plaque laden aorta of human MPO transgenic mice compared to their wild type counterparts (FIG. 3e). In further analyses, a strong correlation ($R^2=0.64$, $p<0.001$) was noted between aortic tissue HCit content versus aortic total cholesterol content (FIG. 3f).

Prior studies demonstrate MPO is catalytically active within human atheroma, as monitored by specific oxidative products formed by MPO (e.g. chlorinated protein and lipid products)[13,39]. Since $SCN^-$ is a preferred substrate for MPO, we next sought to test whether MPO might similarly serve as a source of protein carbamylation within the human artery wall at a site of atherosclerotic plaque. Immunohistochemical analyses were performed on fresh surgical human carotid artery specimens recovered from non-uremic subjects at time of endarterectomy (FIG. 3g). Monoclonal antibodies specific for MPO predominantly demonstrated staining within and around shoulder regions of intermediate atherosclerotic plaques, as well as within cholesterol clefts in more complex lesions. Dual immunofluorescence staining with monoclonal antibodies specific for carbamylated protein demonstrated similar localization patterns, with epitopes co-localized with MPO immunostaining (FIG. 3g). Collectively, these studies are consistent with the MPO—$H_2O_2$—$SCN^-$ system serving as a dominant pathway for promoting protein carbamylation in vivo both within atherosclerotic plaque and at sites of inflammation.

MPO-Mediated Carbamylation of Lipoproteins Confers Multiple Pro-Atherogenic Biological Activities.

Figure 4:
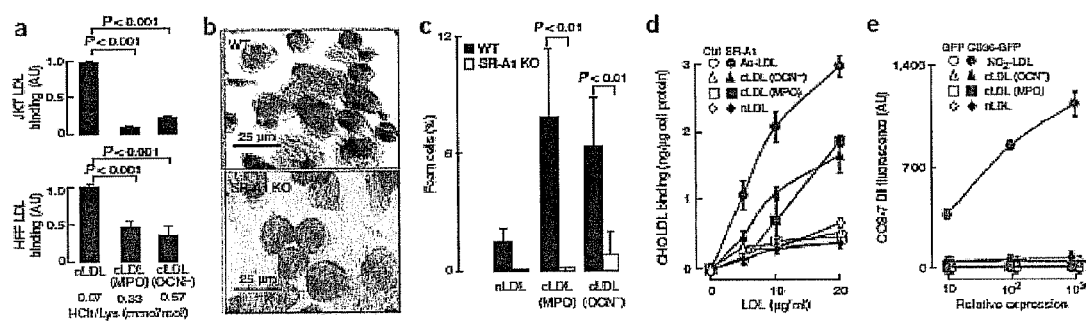
FIG. 4 shows potential pro-atherogenic effects of MPO-catalyzed protein carbamylation. (a) LDL binding to the LDL receptor is impaired following carbamylation by both the $MPO/SCN^-/H_2O_2$ system and $OCN^-$, as monitored by binding of native and carbamylated LDL to Jurkat T cells (JKT) cells transfected with the LDL receptor, and human foreskin fibroblast (HFF) cells after culturing in lipoprotein-deficient serum. LDL binding to JKT cells and HFF cells were determined as described in Supplementary Methods online. (b) LDL modified by the $MPO/SCN^-/H_2O_2$ system induces lipid loading of macrophages from wild-type (WT) mice but not from scavenger receptor class A type 1 null mice (SR-AI-KO). Cells were fixed with 4% formaldehyde and stained with hematoxylin and oil red O. (c) % Foam cells were counted after macrophages were incubated with carbamylated LDL (cLDL) by either the $MPO/SCN^-/H_2O_2$ system or $OCN^-$. Cells containing over 10 lipid droplets were identified as foam cells under microscopy. Data represents as mean±SE for cells in at least 10 fields counted from at least 3 independent experiments. (d, e) Binding of LDL by murine SR-AI (filled symbols) or vector-transfected (open symbols) CHO cells and CD36 (filled symbols) or vector-transfected (open symbols) COS-7 cells as indicated after either no modification (nLDL), carbamylation by either the MPO/SCN$^-$/H$_2$O$_2$ system or OCN$^-$ (as indicated), acetylated LDL (Ac-LDL) or LDL exposed to MPO-generated nitrating oxidants (NO$_2$-LDL) as listed.
Figure 5:
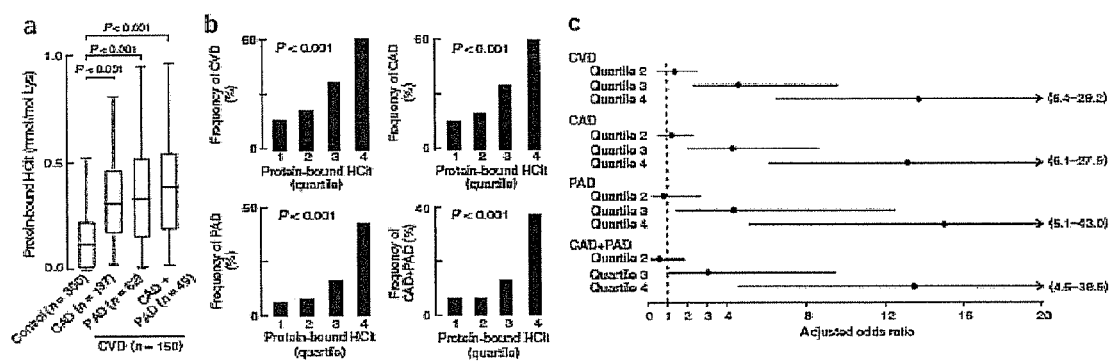
FIG. 5 shows the results from a Case: Control study examining the relationship between plasma levels of protein bound HCit and prevalence of atherosclerotic CVD. Plasma was isolated from sequential subjects undergoing diagnostic cardiac catheterization with CVD (n=150), and age and gender matched control subjects (n=300). (a) Plasma levels of protein bound HCit in subjects with (n=150) and without (n=300) atherosclerotic CVD. (b) Frequency of atherosclerotic CVD, CAD and PAD according to quartiles of protein bound HCit. P values indicated are for trend across quartiles. (c) Odds ratio and 95% confidence interval versus protein bound HCit quartiles for CVD, CAD, PAD and CAD+PAD risks following multilogistic regression. Model consisted of Framingham risk score, estimated glomerular filtration rate by MDRD formula, MPO, C-reactive protein (CRP), and protein bound HCit level.
Figure 6:
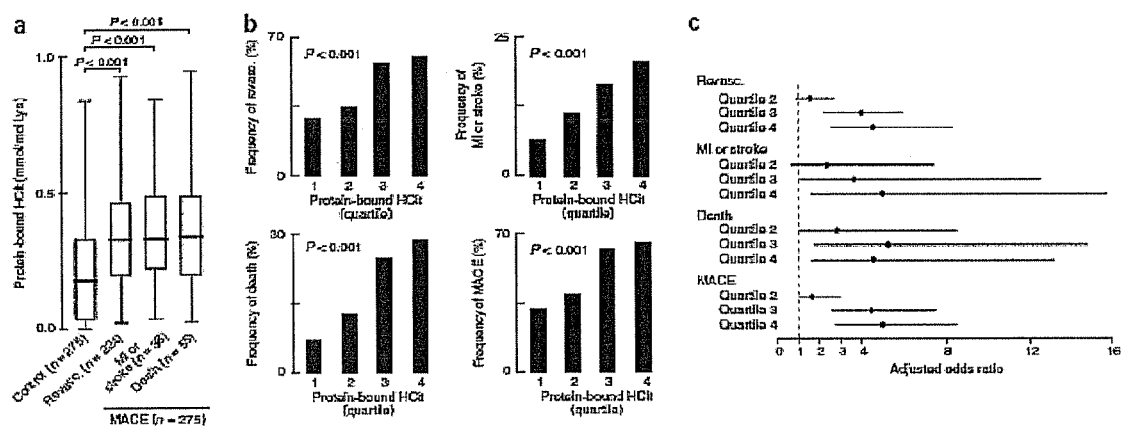
FIG. 6 shows the results from a Case: control study examining the relationship between plasma levels of protein bound HCit and prospective risk for major adverse cardiac event (MACE=revascularization (revasc), myocardial infarction (MI), stroke or death). Plasma was analyzed for protein bound HCit content from case subjects (n=275) who underwent diagnostic cardiac catheterization and experienced a major adverse cardiac event (MACE, the composite of non-fatal MI, stroke, need for revascularization or death) in the 3 year period following study enrollment. Parallel analyses were also performed on plasma from age and gender matched control subjects (n=275) who underwent diagnostic cardiac catheterization and failed to experience a major adverse cardiac event over the ensuing 3 years following study enrollment. (a) Plasma levels of protein bound HCit in subjects with (n=275) and without (n=275) subsequent clinical events. (b) Frequency of clinical events (revascularization, MI or stroke, death, and the composite, MACE) according to quartiles of protein bound HCit. P values indicated are for trend across quartiles. (c) Odds ratio and 95% confidence interval versus protein bound HCit quartiles for incident risk of clinical events (need for revascularization, non-fatal MI or stroke, death or the composite, MACE) following multilogistic regression. Model consisted of Framingham risk score, estimated glomerular filtration rate by MDRD formula, MPO, C-reactive protein (CRP) level and protein bound HCit level.

LDL isolated from uremic patients (ie "uremic" LDL) is reported to possess multiple pro-atherosclerotic activities, presumably as a consequence of carbamylation[3,11,40]. In an analogous fashion, we hypothesized that MPO-catalyzed carbamylation of proteins in the artery wall might similarly confer pro-atherosclerotic properties. To test this hypothesis, we first examined whether carbamylation of LDL by the MPO/$H_2O_2$/$SCN^-$ system inhibited LDL receptor recognition of the modified lipoprotein (FIG. 4a), similar to uremic LDL[3,11,40]. As a control, parallel mass spectrometry studies were performed to confirm that a physiologically relevant degree of protein carbamylation was used (ie protein-bound HCit levels were comparable to that observed for plasma proteins, or <500 μmol HCit/mol lysine; FIGS. 5 and 6). Exposure of LDL to either the MPO/$H_2O_2$/$SCN^-$ system or the potassium salt of $OCN^-$ (a chemical mechanism for promoting carbamylation) markedly attenuated recognition of the lipoprotein by the LDL receptor (FIG. 4a), suggesting that MPO-carbamylated LDL will have delayed clearance and be retained in the artery wall.

We next examined whether carbamylation of LDL conferred an alternative pro-atherogenic biological activity, macrophage scavenger receptor recognition, cholesterol accumulation and foam cell formation. LDL carbamylated by either the MPO/$H_2O_2$/$SCN^-$ system or the potassium salt of $OCN^-$ demonstrated saturable and specific binding (at 4° C.) to mouse peritoneal macrophages (data not shown), whereas incubation at 37° C. resulted in carbamylated lipoprotein uptake, cholesterol accumulation and foam cell formation (FIG. 4b, top panel). Similar results (i.e., binding, uptake and foam cell formation) were observed with peritoneal macrophages from CD36 knockout mice (data not shown), indicating the scavenger receptor CD36 does not participate in carbamylated LDL recognition by macrophages. In contrast, macrophages from scavenger receptor class A type 1 knockout mice (SR-A1KO) failed to bind (at 4° C.) to carbamylated LDL, and consequently, during longer incubations (at 37° C.) showed no evidence of cholesterol accumulation and foam cell formation (FIGS. 4b and 4c). Independent confirmation of carbamylated LDL recognition by the scavenger receptor SR-A1 was obtained in binding studies using either cells stably transfected with either SR-A1 versus vector transfected control cells (FIG. 4d), or the SR-A1 inhibitor fucoidin, which inhibited over 80% of specific binding (data not shown). Similarly, confirmation that carbamylated LDL was not recognized by scavenger receptor CD36 was obtained in separate binding studies employing cells either stably transfected with the scavenger receptor CD36 or GFP as control. While $NO_2LDL$, a known ligand for CD36[14], bound to cells transfected with CD36, carbamylated LDL showed no binding to the CD36 expressing cells (FIG. 4e).

Uremic LDL is reported to possess alternative pro-atherosclerotic biological activities, including both serving as a mitogen for vascular smooth muscle cells and inducting endothelial cell apoptosis[11]. In a separate series of studies, we therefore examined the impact of MPO-catalyzed lipoprotein carbamylation on these processes. While exposure of aortic smooth muscle cells (both human and bovine) to native LDL had no effect on proliferation, incubation with either MPO-carbamylated LDL or LDL carbamylated with reagent $OCN^-$ induced marked smooth muscle cell proliferation. The presence of an SR-A1 inhibitor in culture media, fucoidin, markedly suppressed the degree of proliferation induced, suggesting a role for SR-A1 in facilitating carbamylated LDL dependent vascular smooth muscle cell proliferation In separate studies we tested the hypothesis that physiologically relevant levels of protein carbamylation induced by the MPO—$H_2O_2$—$SCN^-$ system could promote aortic endothelial cell apoptosis, as monitored by both caspase activation and TUNEL assays. Exposure of cells to physiologically relevant levels of carbamylated high density lipoprotein (HDL) resulted in induction of bovine aortic endothelial cells apoptosis. Further, addition of (patho)physiologically relevant levels of $SCN^-$ to the culture medium of aortic endothelial cells incubated with catalytic (nM) levels of MPO and an $H_2O_2$ generating system (glucose/glucose oxidase) demonstrated dose-dependent increases in endothelial cell caspase-3/-7 activation, but only in the presence of all components of the MPO—$H_2O_2$—$SCN^-$ system. In a final series of studies using human coronary artery endothelial cells (HCAECs) and siRNA to the HDL receptor SR-B1, we observed that in contrast to the an anti-apoptotic activity promoted by native HDL interaction with SR-B1 in HCAECs, carbamylated HDL no longer possessed anti-apoptotic activity with HCAECs, suggesting interference of SR-B1 recognition of the modified lipoprotien.

Plasma Levels of Protein Bound Homocitrulline are Independently Associated with Atherosclerotic Cardiovascular Disease.

To more directly examine the potential clinical relevance of protein carbamylation to atherosclerosis in humans, we initially performed a case:control (1:2) study investigating the relationship between systemic levels of protein bound HCit and atherosclerotic CAD prevalence. All subjects included were part of GeneBank, a large (n=10,000) clinical repository generated from sequential consenting subjects undergoing diagnostic left heart catheterization and for whom outcome data is also monitored. Controls (n=300) were defined as subjects without clinical evidence of cardiovascular disease (CVD) and for whom no significant angiographic evidence of atherosclerosis was noted (<50% stenosis in all major coronary vessels) at time of GeneBank entry. Age- and gender-matched cases (n=150) were randomly selected amongst GeneBank subjects with known CVD (defined as documented history of CAD, peripheral artery disease (PAD), myocardial infarction (MI), stroke, revascularization procedure, or angiographic evidence (>50% stenosis) of atherosclerosis in one or more major coronary vessels) at the time of GeneBank enrollment.

Subject clinical and demographic characteristics are detailed in Table 1 below.

SUPPLEMENTARY TABLE 1

Demographics of case/control study 1: protein bound HCit and CVD prevalence

| Characteristic | Controls (n = 300) | Patients with CVD (n = 150) | P value |
|---|---|---|---|
| Age, years | 61 (50-67) | 62 (57-68) | 0.16 |
| Women, % | 64 | 54 | 1.0 |
| Diabetes, % | 14.0 | 39.3 | <0.001 |
| Hypertension, % | 36 | 46 | 0.43 |
| History of smoking, % | 53.3 | 57.3 | 0.79 |
| Current smoking, % | 4.3 | 4.7 | 0.93 |
| Thiocyanate (SCN$^-$), μM | 48.2 (27.2-82.3) | 48.1 (31.3-78.7) | 0.29 |
| LDL cholesterol, mg/dL | 107 (85-130) | 94 (78-121) | 0.01 |
| HDL cholesterol, mg/dL | 49 (40-63) | 45 (36-56) | <0.001 |
| Triglycorides, mg/dL | 117 (84-161) | 142 (105-200) | 0.001 |
| CRP, mg/dL | 2.2 (1.1-5.0) | 3.8 (1.8-7.5) | <0.001 |
| MDRD | 84 (60-102) | 83 (64-103) | 0.22 |
| MPO, nmol/L | 1.03 (0.65-1.59) | 1.06 (0.72-1.52) | 0.51 |

Case: Control study examining the relationship between plasma levels of protein bound HCit and prevalence of atherosclerotic cardiovascular disease (CVD). Plasma was isolated from sequential consenting subjects undergoing diagnostic cardiac catheterization who participate in the GeneBank study. A random sampling of subjects with CVD (n = 150), and age and gender matched control subjects (n = 300) were randomly selected from GeneBank, and plasma samples analyzed. Clinical and laboratory characteristics of subjects are listed.

Abbreviations:

C-reactive protein (CRP);

modification of diet in renal disease (MDRD, an estimate of glomerular filtration rate[12]);

Myeloperoxidase (MPO).

No significant differences were noted in smoking prevalence, plasma thiocyanate levels, or renal function between cases vs. controls. Subjects with CVD had significantly higher levels of plasma protein bound HCit than controls (FIG. 5a). Further, increases in plasma HCit levels dose-dependently were associated with marked increases in the frequency of subjects having CVD, as well as those having either CAD, PAD, or the combination of both CAD and PAD (FIG. 5b). Subjects with plasma protein bound HCit levels in the top quartile of the study population (≥300 μmol HCit/mol lysine) had approximately 7 to 8-fold increase in risk of having clinical or angiographic evidence of CVD, compared to subjects with first quartile (≤30 μmol HCit/mol lysine) levels as shown in Table 2 below.

SUPPLEMENTARY TABLE 2

Case: Control study examining the relationship between plasma levels of protein bound HCit and prevalence of atherosclerotic cardiovascular disease (CVD).
Odds Ratio of Cardiovascular Disease Risk

| Protein bound HCit (mmol/mol Lys) | | Quartile | | | |
|---|---|---|---|---|---|
| | | 1 (≤0.03) | 2 (0.03-0.10) | 3 (0.10-0.30) | 4 (≥0.30) |
| | | OR (95% CI) | | | |
| CVD | Unadjusted | 1.0 | 1.3 (0.7-2.6) | 3.1 (1.6-5.7) | 8.0 (4.2-15.0) |
| | Adjusted | 1.0 | 1.0 (0.6-2.6) | 4.7 (2.3-9.6) | 13.7 (6.4-29.2) |
| PAD | Unadjusted | 1.0 | 1.0 (0.4-2.9) | 2.0 (0.9-5.7) | 0.0 (0.0-20.1) |
| | Adjusted | 1.0 | 0.09 (0.3-2.7) | 4.2 (1.4-12.4) | 14.9 (5.1-43.0) |
| CAD | Unadjusted | 1.0 | 1.1 (0.7-2.8) | 3.1 (1.6-6.0) | 8.3 (1.3-16.0) |
| | Adjusted | 1.0 | 1.1 (0.6-2.3) | 4.2 (2.0-8.6) | 13.0 (6.1-27.9) |
| OAD + PAD | Unadjusted | 1.0 | 1.0 (0.3-3.4) | 2.2 (0.0-0.3) | 0.0 (0.7-25.0) |
| | Adjusted | 1.0 | 0.6 (0.2-1.9) | 3.0 (1.0-9.4) | 13.3 (4.5-38.9) |

Model consisted of Framingham risk score, MPO, MDRD, CRP and protein bound HCit

Plasma was isolated from sequential consenting subjects undergoing diagnostic cardiac catheterization who participated in the GeneBank study. A random sampling of subjects with CVD (n = 150), and a random sampling of age- and gender-matched control subjects (n = 300) were selected and plasma analyzed. Odds ratio and 95% confidence interval versus protein bound HCit quartiles for CVD, coronary artery disease (CAD) peripheral artery disease (PAD) and CAD + PAD is shown. Multilogistic regression model consisted of Framingham risk score, estimated glomerular filtration rate by modification of diet in renal disease (MDRD) formula, myeloperoxidase (MPO), C-reactive protein (CRP), and protein bound HCit level.

Increased HCit levels were similarly associated with increased risk of having CAD, PAD or CAD+PAD. The striking relationship for increased risk of CVD with elevated systemic levels of HCit remained true even following multi-logistic regression analysis following adjustments for traditional cardiac risk factors, estimated glomerular filtration rate, serum MPO levels and C-reactive protein levels, an alternative marker of inflammation (FIG. 5c, and see Table 2). Thus, systemic levels of protein bound HCit demonstrate strong and independent association with CVD prevalence.
Plasma Levels of Protein Bound Homocitrulline Predict Future Risk for Non-Fatal Myocardial Infarction (MI) or Stroke, Need for Revascularization, and Death.

To further investigate the potential clinical significance of systemic indices of protein carbamylation relative to CVD risks in subjects, we performed a second case:control (1:1) study examining the relationship between plasma levels of protein bound HCit and future risk for need for revascularization, non-fatal MI or stroke, or death. Cases (n=275) were GeneBank subjects who experienced documented non-fatal MI, stroke, revascularization procedure or death within 3 years following enrollment. Controls (n=275) were age- and gender-matched subjects randomly selected from the GeneBank population who did not experience a MI, stroke, revascularization procedure or death over the 3 years following enrollment. Subject clinical and demographic characteristics are shown in Table 3 below.

SUPPLEMENTARY TABLE 3

Demographics of case/control study 2: protein bound HCit and future risk of MACE.

| Characteristic | Controls (n = 275) | Patients with MACE (n = 275) | P value |
|---|---|---|---|
| Age, years | 64 (58-71) | 65 (58-72) | 0.45 |
| Women, % | 56.0 | 56.0 | 1.00 |
| Diabetes, % | 22.9 | 43.8 | <0.001 |
| Hypertension, % | 64.5 | 77.2 | 0.001 |
| History of smoking, % | 55.3 | 58.0 | 0.51 |
| Current smoking, % | 5.5 | 4.7 | 0.71 |
| Thiocyanate(SCN$^-$), μM | 50 (33-82) | 47 (27-74) | 0.092 |
| LDL cholesterol, mg/dL | 101 (80-120) | 94 (76-121) | 0.083 |
| HDL cholesterol, mg/dL | 46 (38-57) | 42 (34-52) | <0.001 |
| Triglycerides, mg/dL | 130 (89-180) | 141 (105-210) | 0.009 |
| CRP, mg/dL | 2.6 (1.2-6.0) | 3.1 (1.5-6.5) | 0.11 |
| Creatine, mg/dL | 0.9 (0.8-1.0) | 0.9 (0.8-1.2) | 0.006 |
| MDRD | 83 (60-101) | 79 (58-99) | 0.006 |
| MPO, nmol/L | 0.03 (0.63-1.33) | 1.01 (0.71-1.68) | 0.004 |

Case: Control study 2 examining the relationship between plasma levels of protein bound HCit and prospective risk for major adverse cardiac event (MACE = revascularization revasc), myocardial infarction (MI), stroke or death). Plasma was isolated from sequential consenting subjects undergoing diagnostic cardiac catheterization who participated in the GeneBank study. Plasma was analyzed for protein bound HCit content from a random sampling of subjects (n = 275) who experienced a major adverse cardiac event (MACE, the composite of non-fatal MI, stroke, need for revascularization or death) in the 3-year period following study enrollment. Parallel analyses were also performed on plasma from age and gender-matched control subjects (n = 275) enrolled In GeneBank who underwent diagnostic cardiac catheterization and faild to experience a majar adverse cardiac event over the ensuing 3-years following study enrollment. Clinical and laboratory characteristics of subjects are listed.
Abbrevitations:
C-reactive protein (CRP);
modification of diet in renal disease (MDRD, an estimate of glomerular filtration rate[12]);
Myeloperoxidase (MPO).

No significant differences were noted in smoking prevalence and renal function was slightly lower among cases relative to controls, but still with average creatinine clearance rates within the normal range (see Table 3). Subjects who experienced a major adverse cardiac event (MACE=incident MI, stroke, need for revascularization or death) had significantly higher levels of plasma protein bound HCit than those who did not (FIG. 6a). Further, increases in plasma protein bound HCit levels dose-dependently were associated with marked increases in the frequency of experiencing a revascularization procedure (angioplasty, stent or coronary artery bypass grafting), a non-fatal MI or stroke, death, or the composite adverse outcome (MACE) (FIG. 6b). The relationship between increased risk of experiencing a future non-fatal MI, stroke, revascularization procedure or death and elevated plasma protein bound HCit levels remained significant following adjustments for traditional CVD risk factors, renal function, and both MPO and C-reactive protein levels (FIG. 6c, and see Table 4).

SUPPLEMENTARY TABLE 4

Case: Control study examining the relationship between plasma levels of protein bound HCit and prospective risk for major adverse cardiac event (MACE = revascularization (revasc), myocardial infarction (MI), stroke or death).
Odds Ratio for incident MACE (ravasc, MI, stroke or death) risk

| Protein bound HCit (mmol/ mol Lys) | | Quartile | | |
|---|---|---|---|---|
| | 1 (≤0.12) | 2 (0.12-0.25) | 3 (0.25-0.42) | 4 (≥0.42) |
| | | OR (95% CI) | | |
| Revasc Unadjusted | 1.0 | 1.3 (0.8-2.2) | 3.3 (2.0-5.6) | 3.7 (2.2-6.3) |
| Adjusted | 1.0 | 1.6 (0.9-2.8) | 4.0 (2.2-7.0) | 4.8 (2.6-8.3) |
| MI or Stroke Unadjusted | 1.0 | 1.9 (0.7-5.4) | 3.0 (1.0-8.7) | 4.0 (1.4-11.2) |
| Adjusted | 1.0 | 2.3 (0.7-7.4) | 3.7 (1.1-12.6) | 5.0 (1.6-13.2) |
| Death Unadjusted | 1.0 | 1.9 (0.7-5.1) | 4.3 (1.7-11.2) | 5.4 (2.1-13.7) |
| Adjusted | 1.0 | 2.9 (1.0-8.7) | 5.2 (1.8-14.9) | 4.6 (1.6-13.2) |
| MACE Unadjusted | 1.0 | 1.4 (0.9-2.3) | 3.5 (2.1-5.8) | 4.1 (2.5-6.7) |
| Adjusted | 1.0 | 1.8 (1.0-3.0) | 4.4 (2.5-7.6) | 5.0 (2.8-8.7) |

Model consists of Framingham risk score, MPO, MDRD, CRP and protein bound HCit
Plasma was isolated from sequential consenting subjects undergoing diagnostic cardiac catheterization who participated in the GeneBank study. Plasma was analyzed for protein bound HCit content from a random sampling of subjects (n = 275) who experienced a major adverse cardiac event (MACE, the composite of non-fatal MI, stroke, need for revascularization or death) in the 3-year period following study enrollment. Parallel analyses were also performed on plasma from age and gender matched control subjects (n = 275) enrolled in GeneBank. Control subjects similarly underwent diagnostic cardiac catheterization at time of study enrollment, yet failed to experience a major adverse cardiac event over the ensuing 3 years following study enrollment. Odds ratio and 95% confidence interval versus protein bound HCit quarties for incident risk of clinical events (need for revascularization, non-fetal MI or stroke, death or the composite, MACE) is shown. Multilogistic regression model consisted of Framingham risk score, estimated glomerular filtration rate by modification of diet in renal disease (MDRD) formula, myeloperoxidase (MPO), C-reactive protein (CRP), and protein bound HCit level.

In contrast to the historical belief that carbamylation is a process that only occurs to a significant extent during renal dysfunction and uremia, the present studies unambiguously show that protein carbamylation is catalyzed by the leukocyte heme peroxidase MPO, and that inflammation-driven protein carbamylation is a quantitatively dominant mechanism for carbamylation in vivo and within human atherosclerotic lesions (FIG. 1). A continuum of studies including chemical, cellular, physiological, animal model and clinical investigations support the conclusion that protein carbamylation is a biochemical pathway intrinsic to inflammation and the pathophysiology of atherosclerosis. MPO-catalyzed carbamylation of proteins is shown both to occur in human atherosclerotic plaque to a much greater extent than normal arterial tissues, as well as to confer multiple pro-atherosclerotic biological activities, such as impairment in LDL receptor recognition of its lipoprotein, scavenger receptor recognition leading to cholesterol accumulation and foam cell formation, enhanced endothelial cell apoptosis, and induction of vascular smooth muscle cell proliferation. The strong and independent relationship between systemic measures of protein carbamylation and both CAD prevalence and future risks for major adverse cardiac events is consistent with a role for carbamylation as a pathophysiological participant in atherosclerosis. The present studies also suggest that plasma levels of protein bound HCit may serve as a clinically valuable prognostic tool with which to risk stratify subjects independent of traditional cardiovascular risk factors, renal function, and levels of the inflammation biomarkers MPO and C-reactive protein.

Another remarkable aspect of the present studies is the underlying chemical mechanism identified for MPO-catalyzed protein carbamylation—the $MPO/H_2O_2/SCN^-$ system of leukocytes. The pseudo halide $SCN^-$ is a relatively abundant anion in plasma, with systemic levels influenced by dietary intake of foods high in $SCN^-$, such as milk products, almonds, cruciferous vegetables and certain fruits[29,31]. In addition, $SCN^-$ is markedly increased in smokers, and has been used as a means to quantify smoking exposure, both primary and environmental (second hand), particularly in the setting of nicotine supplementation where cotinine levels are not dependable[30,43]. Interestingly, while plasma $SCN^-$ levels were significantly higher within active smokers (over 3-fold; p<0.001) in both cohorts examined in the present study (e.g., for combined cohorts, $SCN^-$ (μM) median (interquartile range) 46.9 (26.6-77.4) versus 158.4 (70.6-234.1) for non-smokers versus smokers, respectively), elevated $SCN^-$ levels by themselves were not predictive of atherosclerotic CAD risks (Supplementary Information, Tables 1 and 3). These results are consistent with a requirement of the carbamylation process itself to render a molecular target atherogenic, a process that requires each component of the $MPO-H_2O_2-SCN^-$ system in the same compartment, such as the vessel wall. Interestingly, within the combined study cohorts examined, protein bound HCit levels in smokers with either prevalent CAD or future risk for MACE were markedly higher than those in smokers without either CAD or future MACE risk (P<0.001 for both comparisons). While the results of both case control clinical studies demonstrate the potential general prognostic utility of systemic protein carbamylation measures as a gauge of atherosclerotic CAD risks in smoker and non-smoker alike, they also suggest an even stronger prognostic value within smokers. The present findings may thus help explain part of the underlying mechanisms that contribute to the enhanced cardiovascular risks associated with tobacco use. Further, monitoring of systemic protein bound HCit levels may serve as a quantitative index with which to gauge overall reductions in vascular inflammation and cardiovascular risks that accompany smoking cessation. Further studies exploring the impact on this molecular process in smokers and non-smokers alike are warranted.

REFERENCES

1. Erill, S., Calvo, R. & Carlos, R. Plasma protein carbamylation and decreased acidic drug protein binding in uremia. *Clin Pharmacol Ther* 27, 612-8 (1980).
2. Fluckiger, R., Harmon, W., Meier, W., Loo, S. & Gabbay, K. H. Hemoglobin carbamylation in uremia. *N Engl J Med* 304, 823-7 (1981).
3. Horkko, S., Huttunen, K., Kervinen, K. & Kesaniemi, Y. A. Decreased clearance of uraemic and mildly carbamylated low-density lipoprotein. *Eur J Clin Invest* 24, 105-13 (1994).
4. Kraus, L. M. & Kraus, A. P., Jr. Carbamoylation of amino acids and proteins in uremia. *Kidney Int Suppl* 78, S102-7 (2001).
5. Stark, G. R., Stein, W. H. & Moore, S. Reactions of the cyanante present in aqueous urea with amino acids and proteins. *J Biol Chem* 235, 3177-81 (1960).
6. Bobb, D. & Hofstee, B. H. Gel isoelectric focusing for following the successive carbamylations of amino groups in chymotrypsinogen A. *Anal Biochem* 40, 209-17 (1971).
7. Stark, G. R. Reactions Of Cyanate With Functional Groups Of Proteins. Ii. Formation, Decomposition, And Properties Of N-Carbamylimidazole. *Biochemistry* 4, 588-95 (1965).
8. Stim, J. et al. Factors determining hemoglobin carbamylation in renal failure. *Kidney Int* 48, 1605-10 (1995).
9. Lhotta, K., Schlogl, A., Uring-Lambert, B., Kronenberg, F. & Konig, P. Complement C4 phenotypes in patients with end-stage renal disease. *Nephron* 72, 442-6 (1996).
10. Mun, K. C. & Golper, T. A. Impaired biological activity of erythropoietin by cyanate carbamylation. *Blood Purif* 18, 13-7 (2000).
11. Ok, E., Basnakian, A. G., Apostolov, E. O., Barri, Y. M. & Shah, S. V. Carbamylated low-density lipoprotein induces death of endothelial cells: a link to atherosclerosis in patients with kidney disease. *Kidney Int* 68, 173-8 (2005).
12. Nicholls, S. J. & Hazen, S. L. Myeloperoxidase and cardiovascular disease. *Arterioscler Thromb Vasc Biol* 25, 1102-11 (2005).
13. Hazen, S. L. & Heinecke, J. W. 3-Chlorotyrosine, a specific marker of myeloperoxidase-catalyzed oxidation, is markedly elevated in low density lipoprotein isolated from human atherosclerotic intima. *J Clin Invest* 99, 2075-81 (1997).
14. Podrez, E. A., Schmitt, D., Hoff, H. F. & Hazen, S. L. Myeloperoxidase-generated reactive nitrogen species convert LDL into an atherogenic form in vitro. *J Clin Invest* 103, 1547-60 (1999).
15. Zhang, R. et al. Association between myeloperoxidase levels and risk of coronary artery disease. *Jama* 286, 2136-42 (2001).
16. Brennan, M. L. et al. Prognostic value of myeloperoxidase in patients with chest pain. *N Engl J Med* 349, 1595-604 (2003).
17. Asselbergs, F. W., Reynolds, W. F., Cohen-Tervaert, J. W., Jessurun, G. A. & Tio, R. A. Myeloperoxidase polymorphism related to cardiovascular events in coronary artery disease. *Am J Med* 116, 429-30 (2004).
18. McMillen, T. S., Heinecke, J. W. & LeBoeuf, R. C. Expression of human myeloperoxidase by macrophages promotes atherosclerosis in mice. *Circulation* 111, 2798-804 (2005).
19. Castellani, L. W., Chang, J. J., Wang, X., Lusis, A. J. & Reynolds, W. F. Transgenic mice express human MPO −463G/A alleles at atherosclerotic lesions, developing hyperlipidemia and obesity in −463G males. *J Lipid Res* 47, 1366-77 (2006).
20. Abu-Soud, H. M. & Hazen, S. L. Nitric oxide is a physiological substrate for mammalian peroxidases. *J Biol Chem* 275, 37524-32 (2000).
21. Eiserich, J. P. et al. Myeloperoxidase, a leukocyte-derived vascular NO oxidase. *Science* 296, 2391-4 (2002).
22. Baldus, S. et al. Myeloperoxidase enhances nitric oxide catabolism during myocardial ischemia and reperfusion. *Free Radic Biol Med* 37, 902-11 (2004).
23. Vita, J. A. et al. Serum myeloperoxidase levels independently predict endothelial dysfunction in humans. *Circulation* 110, 1134-9 (2004).

24. Zheng, L. et al. Apolipoprotein A-I is a selective target for myeloperoxidase-catalyzed oxidation and functional impairment in subjects with cardiovascular disease. *J Clin Invest* 114, 529-41 (2004).
25. Shao, B. et al. Tyrosine 192 in apolipoprotein A-I is the major site of nitration and chlorination by myeloperoxidase, but only chlorination markedly impairs ABCA1-dependent cholesterol transport. *J Biol Chem* 280, 5983-93 (2005).
26. Zheng, L. et al. Localization of nitration and chlorination sites on apolipoprotein A-I catalyzed by myeloperoxidase in human atheroma and associated oxidative impairment in ABCA1-dependent cholesterol efflux from macrophages. *J Biol Chem* 280, 38-47 (2005).
27. Wu, Z., Wagner, M. A., Zheng, L., Parks, J. S., Shy III, S. M., Smith, J. D., Gogonea, V., & Hazen, S. L. The refined structure of nascent HDL reveals a key functional domain for particle maturation and dysfunction. *Nature Structural & Molecular Biology*, (2007), in press.
28. Wever, R., Kast, W. M., Kasinoedin, J. H. & Boelens, R. The peroxidation of thiocyanate catalysed by myeloperoxidase and lactoperoxidase. *Biochim Biophys Acta* 709, 212-9 (1982).
29. Olea, F. & Parras, P. Determination of serum levels of dietary thiocyanate. *J Anal Toxicol* 16, 258-60 (1992).
30. Husgafvel-Pursiainen, K., Sorsa, M., Engstrom, K. & Einisto, P. Passive smoking at work: biochemical and biological measures of exposure to environmental tobacco smoke. *Int Arch Occup Environ Health* 59, 337-45 (1987).
31. van Dalen, C. J., Whitehouse, M. W., Winterbourn, C. C. & Kettle, A. J. Thiocyanate and chloride as competing substrates for myeloperoxidase. *Biochem J* 327 (Pt 2), 487-92 (1997).
32. Kersten, H. W., Moorer, W. R. & Wever, R. Thiocyanate as a cofactor in myeloperoxidase activity against *Streptococcus mutans. J Dent Res* 60, 831-7 (1981).
33. Arlandson, M. et al. Eosinophil peroxidase oxidation of thiocyanate. Characterization of major reaction products and a potential sulfhydryl-targeted cytotoxicity system. *J Biol Chem* 276, 215-24 (2001).
34. Stark, G. R. On the reversible reaction of cyanate with sulfhydryl groups and the determination Of NH2-terminal cysteine and cystine in proteins. *J Biol Chem* 239, 1411-4 (1964).
35. Stark, G. R. & Smyth, D. G. The use of cyanate for the determination of $NH_2$-terminal residues in proteins. *J Biol Chem* 238, 214-26 (1963).
36. Brennan, M. L. et al. A tale of two controversies: defining both the role of peroxidases in nitrotyrosine formation in vivo using eosinophil peroxidase and myeloperoxidase-deficient mice, and the nature of peroxidase-generated reactive nitrogen species. *J Biol Chem* 277, 17415-27 (2002).
37. Zhang, R. et al. Myeloperoxidase functions as a major enzymatic catalyst for initiation of lipid peroxidation at sites of inflammation. *J Biol Chem* 277, 46116-22 (2002).
38. Kumar, A. P., Piedrafita, F. J. & Reynolds, W. F. Peroxisome proliferator-activated receptor gamma ligands regulate myeloperoxidase expression in macrophages by an estrogen-dependent mechanism involving the −463GA promoter polymorphism. *J Biol Chem* 279, 8300-15 (2004).
39. Thukkani, A. K. et al. Identification of alpha-chloro fatty aldehydes and unsaturated lysophosphatidylcholine molecular species in human atherosclerotic lesions. *Circulation* 108, 3128-33 (2003).
40. Horkko, S., Savolainen, M. J., Kervinen, K. & Kesaniemi, Y. A. Carbamylation-induced alterations in low-density lipoprotein metabolism. *Kidney Int* 41, 1175-81 (1992).
41. Sugiyama, S. et al. Hypochlorous acid, a macrophage product, induces endothelial apoptosis and tissue factor expression: involvement of myeloperoxidase-mediated oxidant in plaque erosion and thrombogenesis. *Arterioscler Thromb Vasc Biol* 24, 1309-14 (2004).
42. Yang, J., Cheng, Y., Ji, R. & Zhang, C. A novel model of inflammatory neointima formation reveals a potential role of myeloperoxidase in neointimal hyperplasia. *Am J Physiol Heart Circ Physiol* (2006).
43. Hill, P., Haley, N. J. & Wynder, E. L. Cigarette smoking: carboxyhemoglobin, plasma nicotine, cotinine and thiocyanate vs self-reported smoking data and cardiovascular disease. *J Chronic Dis* 36, 439-49 (1983).
44. Markwell, M. A., Haas, S. M., Bieber, L. L. & Tolbert, N. E. A modification of the Lowry procedure to simplify protein determination in membrane and lipoprotein samples. *Analytical Biochemistry.* 87, 206-10 (1978).
45. Podrez, E. A. et al. Macrophage scavenger receptor CD36 is the major receptor for LDL modified by monocyte-generated reactive nitrogen species. *J Clin Invest* 105, 1095-108 (2000).
46. Anderson, K. M., Odell, P. M., Wilson, P. W. & Kannel, W. B. Cardiovascular disease risk profiles. *Am Heart J* 121, 293-8 (1991).
47. Stoves, J., Lindley, E. J., Barnfield, M. C., Burniston, M. T. & Newstead, C. G. MDRD equation estimates of glomerular filtration rate in potential living kidney donors and renal transplant recipients with impaired graft function. *Nephrol Dial Transplant* 17, 2036-7 (2002).

Example 2

Carbamylated Albumin and Carbamylated Immunoglobulin as Biomarkers for CVD

Sequential patients undergoing diagnostic cardiac catheterization were enrolled for the study. The first 25 subjects with known CVD or angiographically documented (>50% stenosis) coronary artery disease were considered cases. The first 25 subjects without known CVD and no angiographic evidence of coronary artery disease (<30% stenosis) were considered Non-CVD Subjects. Plasma levels of protein bound homocitrulline and free homocitrulline were each determined by LC/ESI/MS/MS methods. In addition, plasma from the same samples were rendered free of LDL by immunoprecipitation of apoB-100 from specimens (LDL-free plasma), and then protein bound homocitrulline levels determined. Finally, two abundant proteins in plasma, albumin and IgG, were individually isolated (albumin with immobilized anti-HAS mAb, and IgG with immobilized protein A), were isolated from each sample, and then their content of carbamyllysine (homocitrulline) determined by LC/ESI/MS/MS. The results are shown below in Table 5 below. Levels of protein bound homocitrullline are expressed as a product/precursor ratio relative to the amino acid lysine, which was simultaneously quantified by LC/ESI/MS/MS based methods.

TABLE 5

| | CVD Subjects (n = 12) | Non-CVD Subjects (n = 12) | |
|---|---|---|---|
| | Protein-bound Homocitrulline (mmol/mol lysine) | | P |
| Plasma | 0.61 +/− 0.29 | 0.22 +/− 0.20 | <0.001 |
| LDL-free Plasma | 0.58 +/− 0.35 | 0.25 +/− 0.18 | <0.001 |
| albumin | 1.23 +/− 0.42 | 0.34 +/− 0.31 | <0.001 |
| IgG | 0.89 +/− 0.65 | 0.47 +/− 0.12 | <0.001 |
| Free Homocitrulline Nanomolar | 345 +/− 156 | 150 +/− 119 | <0.001 |

These results demonstrate that plasma levels of free and protein bound HCit are increased in patients with CVD. These results also demonstrate that the proteins within plasma that are the primary targets of carbamylation (as monitored by protein bound homocitrulline) are not LDL, since levels of homocitrulline remain unchanged by removal of LDL from plasma. These results are consistent with Western data (not shown) using antibodies specific to homocitrulline that show a number of slecect proteins in plasma serve as targets for carbamyllation, and that albumin and immunoglobulins are amongst the most abundant carbamylation targets in plasma. These results also demonstrate that Carbamyllysine (homocitrulline) content within both albumin and IgG each serve as predictors of CVD risk.

Example 3

Effect of Simvastatin on Plasma Levels of Homocitrulline (pM)

This study was intended to evaluate the effect of statin therapy on homocitrulline levels. Specimens came from archival materials from a randomized, double-blind, parallel-group, 4-arm, placebo-controlled, multi-center study conducted in 1997. Prior to randomization, subjects underwent a 4-week diet/placebo run-in period. Eligible patients were then randomized to 1 of 4 treatments (ratio 1:1:1:1): placebo, simvastatin 20, 40, or 80 mg, and received 6 weeks of treatment. One hundred and eighty eight out of 195 enrolled men and women completed the study. Subjects were required to have elevated TG (300 to 900 mg/dL), and many had comorbidities associated with the metabolic syndrome; however, though those with morbid obesity, uncontrolled hypertension, or severe hyperlipidemia were excluded. Archived serum and/or plasma that were drawn predose on Day 1 and on Day 42 were used in this analysis. The results are depicted in Table 6 below.

TABLE 6

| Treatment | N | Median Baseline (SD) | Median % Change (SD) | p-Value vs Placebo |
|---|---|---|---|---|
| Placebo | 42 | 213.75 (300.81) | −12.31 (123.95) | |
| Simvastatin 20 mg | 39 | 84.31 (338.61) | −100.0 (102.67) | 0.216 |
| Simvastatin 40 mg | 42 | 233.64 (381.13) | −100.0 (67.77) | 0.041 |
| Simvastatin 80 mg | 40 | 260.31 (395.70) | −63.44 (89.63) | 0.114 |
| Simvastatin combined | 121 | 194.70 (381.13) | −100.0 (84.03) | 0.040 |

These data show that homocitrulline levels are modulated by statin therapy. Dramatic reductions in homocitrulline levels were noted in subjects following statin therapy. These results suggest that free and protein bound homocitrulline may serve as a potential target for adjusting the anti-inflammatory and anti-cardiovascular risk benefit activities of statins.

What is claimed in:

1. A method of identifying a subject at risk of experiencing a complication of cardiovascular disease near term, comprising
determining a level of peptide bound homocitrulline present in a carbamylated marker in a bodily fluid sample, wherein the carbamylated marker is selected from: carbamylated albumin; carbamylated fibrinogen; carbamylated immunoglobulin; and carbamylated apolipoprotein A, by:
contacting the bodily fluid sample of the subject with a first antibody that is immunoreactive with one or more of the carbamylated markers, thereby immunoprecipitating a select protein sample; and
contacting the immunoprecipitated select protein sample with a second antibody that is immunoreactive with peptide bound homocitrulline; and assaying for a complex formed between the select protein sample and the second antibody to determine the level of peptide bound homocitrulline present in the carbamylated marker;
wherein the bodily fluid sample is blood, serum, plasma, saliva or urine; and
wherein the subject whose level of peptide bound homocitrulline is elevated as compared to a reference value based on a level of peptide bound homocitrulline in a corresponding carbamylated marker in a comparable bodily fluid sample from a reference cohort is at risk of experiencing a complication of cardiovascular disease within an ensuing three years.

2. The method of claim 1, wherein the subject is a non-smoker.

3. The method of claim 1, wherein the subject does not have clinical evidence of cardiovascular disease.

4. The method of claim 1, wherein the subject does not have clinical evidence of renal disease.

5. The method of claim 1, wherein the subject whose level of peptide bound homocitrulline is elevated as compared to a reference value based on the level of peptide bound homocitrulline in comparable bodily fluids from a reference cohort is at risk of experiencing a complication of cardiovascular disease within an ensuing 6 months.

6. A method of determining if a subject with natural kidney function is at risk of having or at risk of developing cardiovascular disease in the future, comprising:
determining a level of peptide bound homocitrulline present in a carbamylated marker, in a bodily fluid sample of the subject, wherein the carbamylated marker is selected from: carbamylated albumin; carbamylated fibrinogen; carbamylated immunoglobulin; and carbamylated apolipoprotein A, by:
contacting the bodily fluid sample of the subject with a first antibody that is immunoreactive with one or more of the carbamylated markers, thereby immunoprecipitating a select protein sample; and
contacting the immunoprecipitated select protein sample with a second antibody that is immunoreactive with peptide bound homocitrulline; and assaying for a complex formed between the select protein sample and the second antibody to the determine the level of peptide bound homocitrulline present in the carbamylated marker;

wherein the bodily fluid sample is blood, serum, plasma, urine, or saliva, and wherein the subject whose level of peptide bound homocitrulline, in the bodily fluid sample is elevated as compared to a reference value based on a level of peptide bound homocitrulline in a corresponding carbamylated marker in a comparable bodily fluid sample from a reference cohort is at risk of having cardiovascular disease.

* * * * *

UNITED STATES PATENT AND TRADEMARK OFFICE
CERTIFICATE OF CORRECTION

PATENT NO.         : 9,086,425 B2
APPLICATION NO.    : 12/674715
DATED              : July 21, 2015
INVENTOR(S)        : Stanley L. Hazen and Zeneng Wang Page 1 of 1

It is certified that error appears in the above-identified patent and that said Letters Patent is hereby corrected as shown below:

In the Specification

In Column 1, Lines 6-9 should read:
This invention was made with government support under HL070621, HL076491 and HL077107 awarded by the National Institutes of Health. The government has certain rights in the invention.

Signed and Sealed this
Twentieth Day of October, 2020

Andrei Iancu
*Director of the United States Patent and Trademark Office*